(12) United States Patent  
Alexander et al.

(10) Patent No.: US 9,949,814 B2  
(45) Date of Patent: Apr. 24, 2018

(54) SYSTEMS, TOOLS, AND METHODS FOR TREATMENTS OF PELVIC CONDITIONS

(75) Inventors: James A. Alexander, Excelsior, MN (US); Chaouki A. Khamis, Edina, MN (US); Thomas O. Viker, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 237 days.

(21) Appl. No.: 13/825,997

(22) PCT Filed: Sep. 29, 2011

(86) PCT No.: PCT/US2011/053985  
§ 371 (c)(1),  
(2), (4) Date: Mar. 26, 2013

(87) PCT Pub. No.: WO2012/050973  
PCT Pub. Date: Apr. 19, 2012

(65) Prior Publication Data  
US 2013/0190558 A1     Jul. 25, 2013

Related U.S. Application Data

(60) Provisional application No. 61/387,751, filed on Sep. 29, 2010, provisional application No. 61/502,694, (Continued)

(51) Int. Cl.  
*A61B 1/32*     (2006.01)  
*A61F 2/00*     (2006.01)  
(Continued)

(52) U.S. Cl.  
CPC ............. *A61F 2/0063* (2013.01); *A61B 1/32* (2013.01); *A61B 17/0206* (2013.01);  
(Continued)

(58) Field of Classification Search  
CPC .......... A61B 1/32; A61B 1/303; A61B 17/02; A61B 17/0206; A61B 17/0293  
(Continued)

(56) References Cited

U.S. PATENT DOCUMENTS

| 202,813 A | 4/1878 | Hall |
|---|---|---|
| 447,761 A | 3/1891 | Clough |

(Continued)

FOREIGN PATENT DOCUMENTS

| GB | 2 424 585 | 10/2006 |
|---|---|---|
| WO | WO2002/078552 | 10/2002 |

(Continued)

OTHER PUBLICATIONS

Tyco Healthcare, "IVS Tunneller," ICS/IUGA Sump., pp. 1-4, (2001).

(Continued)

*Primary Examiner* — Eduardo C Robert  
*Assistant Examiner* — Michelle C Eckman  
(74) *Attorney, Agent, or Firm* — Brake Hughes Bellermann LLP

(57) ABSTRACT

Described are surgical procedure systems, devices, tools, and methods, useful for treating pelvic conditions in a male or female, involving an expansion member.

18 Claims, 16 Drawing Sheets

Related U.S. Application Data filed on Jun. 29, 2011, provisional application No. 61/515,685, filed on Aug. 5, 2011, provisional application No. 61/515,638, filed on Aug. 5, 2011.

(51) Int. Cl.
| | | |
|---|---|---|
| *A61B 17/02* | (2006.01) | |
| *A61F 6/08* | (2006.01) | |
| *A61B 90/30* | (2016.01) | |
| *A61B 17/42* | (2006.01) | |
| *A61B 17/00* | (2006.01) | |

(52) U.S. Cl.
CPC .......... *A61B 17/0293* (2013.01); *A61B 90/30* (2016.02); *A61F 2/0045* (2013.01); *A61F 6/08* (2013.01); *A61B 17/42* (2013.01); *A61B 2017/00734* (2013.01); *A61B 2090/306* (2016.02); *A61B 2090/309* (2016.02)

(58) Field of Classification Search
USPC .................. 600/201, 214, 219–225, 235
See application file for complete search history.

(56) References Cited

U.S. PATENT DOCUMENTS

| | | | |
|---|---|---|---|
| 4,010,740 A | | 3/1977 | Littorin |
| 4,130,113 A | * | 12/1978 | Graham .................. 600/224 |
| 4,834,067 A | * | 5/1989 | Block ...................... 600/184 |
| 5,081,983 A | * | 1/1992 | Villalta et al. ............ 600/224 |
| 5,112,344 A | | 5/1992 | Petros |
| 5,183,032 A | * | 2/1993 | Villalta et al. ............ 600/224 |
| 5,337,736 A | | 8/1994 | Reddy |
| 5,611,515 A | | 3/1997 | Benderev et al. |
| 5,683,349 A | | 11/1997 | Makower et al. |
| 5,842,478 A | | 12/1998 | Benderev et al. |
| 5,860,425 A | | 1/1999 | Benderev et al. |
| 5,873,820 A | * | 2/1999 | Norell ...................... A61B 1/32 600/220 |
| 5,899,909 A | | 5/1999 | Claren et al. |
| 5,944,732 A | | 8/1999 | Raulerson et al. |
| 6,039,686 A | | 3/2000 | Kovac |
| 6,042,534 A | | 3/2000 | Gellman et al. |
| 6,110,101 A | | 8/2000 | Tihon et al. |
| 6,312,443 B1 | * | 11/2001 | Stone ....................... 606/198 |
| 6,338,738 B1 | * | 1/2002 | Bellotti .................. A61B 17/0206 600/201 |
| 6,354,995 B1 | * | 3/2002 | Hoftman et al. ........... 600/219 |
| 6,364,832 B1 | * | 4/2002 | Propp ...................... A61B 1/303 600/201 |
| 6,432,048 B1 | | 8/2002 | Francois |
| 6,612,977 B2 | | 9/2003 | Staskin et al. |
| 6,641,525 B2 | | 11/2003 | Rocheleau et al. |
| 6,648,921 B2 | | 11/2003 | Anderson et al. |
| 6,691,711 B2 | | 2/2004 | Raz et al. |
| 7,025,063 B2 | | 4/2006 | Snitkin et al. |
| 7,182,730 B2 | * | 2/2007 | Fehling ...................... 600/224 |
| 7,303,525 B2 | | 12/2007 | Watwschke et al. |
| 7,347,812 B2 | | 3/2008 | Mellier |
| 7,351,197 B2 | | 4/2008 | Montpetit et al. |
| 7,500,945 B2 | | 3/2009 | Cox et al. |
| 8,152,721 B2 | * | 4/2012 | Michaeli et al. ........... 600/224 |
| 8,409,087 B2 | * | 4/2013 | Ames et al. ................ 600/210 |
| 8,517,914 B2 | | 8/2013 | Anderson et al. |
| 8,636,654 B2 | * | 1/2014 | Protopsaltis ............. 600/201 |
| 2002/0147382 A1 | | 10/2002 | Neisz et al. |
| 2004/0143163 A1 | * | 7/2004 | Palmer et al. ............. 600/204 |
| 2005/0080320 A1 | * | 4/2005 | Lee et al. .................. 600/214 |
| 2005/0215862 A1 | * | 9/2005 | Larson et al. ............. 600/201 |
| 2006/0004261 A1 | * | 1/2006 | Douglas ............. A61B 17/0218 600/210 |
| 2006/0069315 A1 | * | 3/2006 | Miles .................... A61B 5/0488 600/219 |
| 2006/0074278 A1 | * | 4/2006 | Petit et al. ................. 600/224 |
| 2006/0106416 A1 | * | 5/2006 | Raymond et al. ........... 606/198 |
| 2006/0205995 A1 | | 9/2006 | Browning |
| 2007/0043264 A1 | * | 2/2007 | Gillis et al. ............... 600/184 |
| 2007/0118023 A1 | * | 5/2007 | Smith et al. .............. 600/219 |
| 2008/0207988 A1 | * | 8/2008 | Hanes ......................... 600/37 |
| 2008/0214898 A1 | * | 9/2008 | Warren ..................... 600/210 |
| 2009/0018400 A1 | * | 1/2009 | Raymond et al. ......... 600/224 |
| 2009/0069634 A1 | * | 3/2009 | Larkin .................... 600/222 |
| 2009/0182203 A1 | * | 7/2009 | Hartnick et al. ........... 600/219 |
| 2009/0275802 A1 | * | 11/2009 | Hawkes et al. ............ 600/219 |
| 2009/0326331 A1 | * | 12/2009 | Rosen ...................... 600/224 |
| 2010/0081884 A1 | * | 4/2010 | Eckman .................. 600/205 |
| 2010/0217088 A1 | * | 8/2010 | Heiges et al. ............ 600/207 |
| 2010/0217090 A1 | * | 8/2010 | Heiges et al. ............ 600/217 |
| 2010/0280627 A1 | * | 11/2010 | Hanes, II ................. 623/23.72 |
| 2010/0298630 A1 | | 11/2010 | Wignall |
| 2011/0034777 A1 | * | 2/2011 | Ames .................. A61B 17/025 600/206 |
| 2011/0046448 A1 | * | 2/2011 | Paolitto et al. ............ 600/201 |
| 2011/0137128 A1 | * | 6/2011 | Poo ........................ A61B 17/02 600/206 |
| 2012/0010472 A1 | * | 1/2012 | Spann ...................... 600/214 |
| 2012/0016185 A1 | | 1/2012 | Sherts et al. |
| 2012/0316399 A1 | * | 12/2012 | Muzzammel et al. ........ 600/221 |
| 2013/0006061 A1 | * | 1/2013 | Alexander et al. ......... 600/235 |
| 2013/0035555 A1 | * | 2/2013 | Alexander et al. ......... 600/207 |
| 2013/0060095 A1 | * | 3/2013 | Bouquet .................. 600/208 |
| 2013/0090533 A1 | * | 4/2013 | Jaeger ..................... 600/224 |
| 2013/0109910 A1 | * | 5/2013 | Alexander et al. ........... 600/37 |
| 2013/0158359 A1 | * | 6/2013 | Predick et al. ........... 600/224 |
| 2013/0225936 A1 | * | 8/2013 | Alexander et al. ......... 600/235 |
| 2013/0261402 A1 | * | 10/2013 | Hawkins et al. ........... 600/214 |
| 2013/0317301 A1 | * | 11/2013 | Deitch et al. ............. 600/202 |
| 2014/0052143 A1 | * | 2/2014 | Deitch et al. ............. 606/119 |
| 2014/0324072 A1 | * | 10/2014 | Harari et al. ............. 606/139 |

FOREIGN PATENT DOCUMENTS

| | | |
|---|---|---|
| WO | WO2007/097994 | 8/2007 |
| WO | WO2007/149348 | 12/2007 |
| WO | WO2007/149555 | 12/2007 |
| WO | WO2008/057261 | 5/2008 |
| WO | WO2011/082350 | 7/2011 |

OTHER PUBLICATIONS

Tyco Healthcare, "IVS Tunneller," ICS/IUGA Symp., pp. 1-4, (2002).
Winters, et al "Abdominal Sacral Colpopexy and Abdominal Enterocele Repair in the Management of Vaginal Vault Prolapse," Urology 56 (Suppl 6A) pp. 55-63, (2000).
Paraiso et al, "Laparoscopic Surgery for Enterocele, Vaginal Apex Prolapse and Rectocele," Int Urogynecol J, pp. 223-229, (1999).

\* cited by examiner

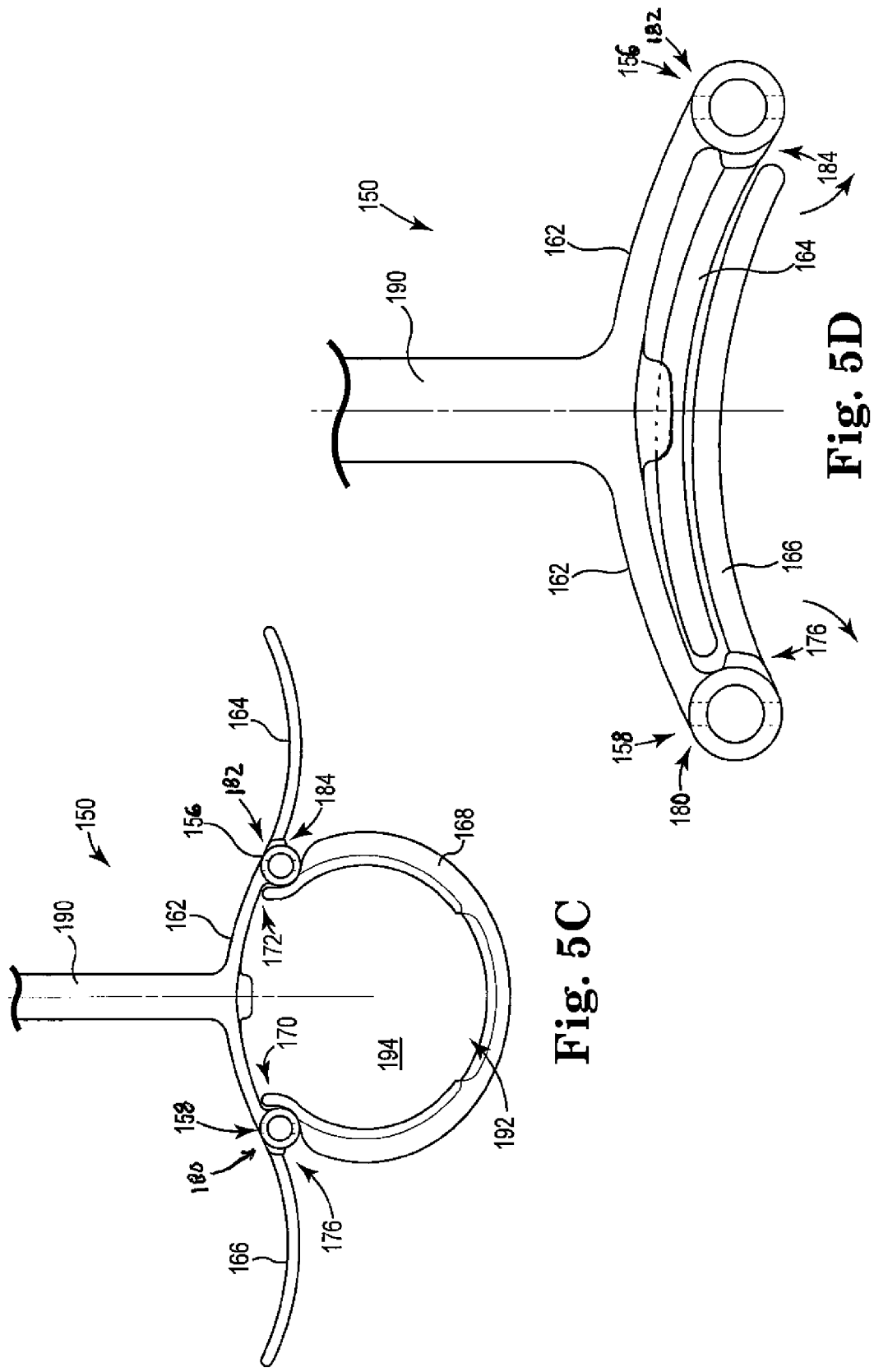

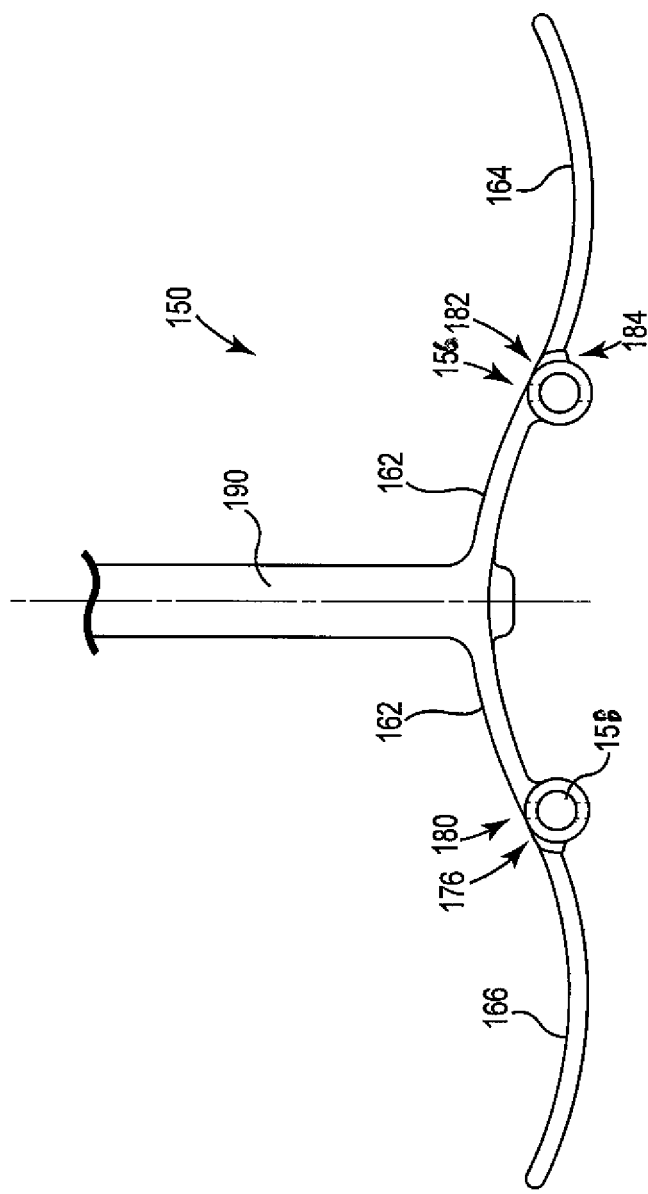

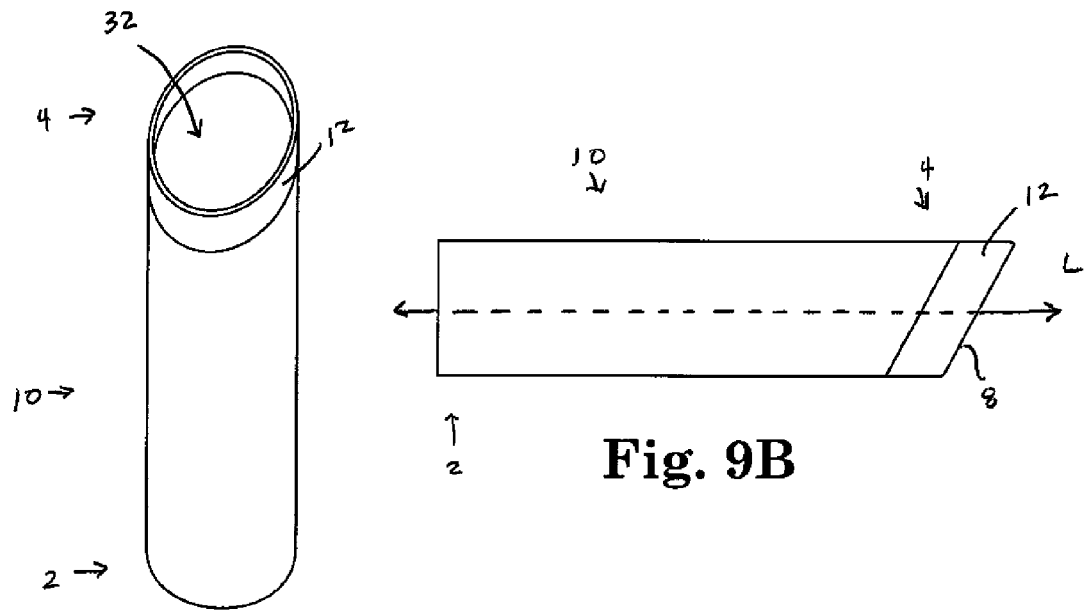
Fig. 9A
Fig. 9B
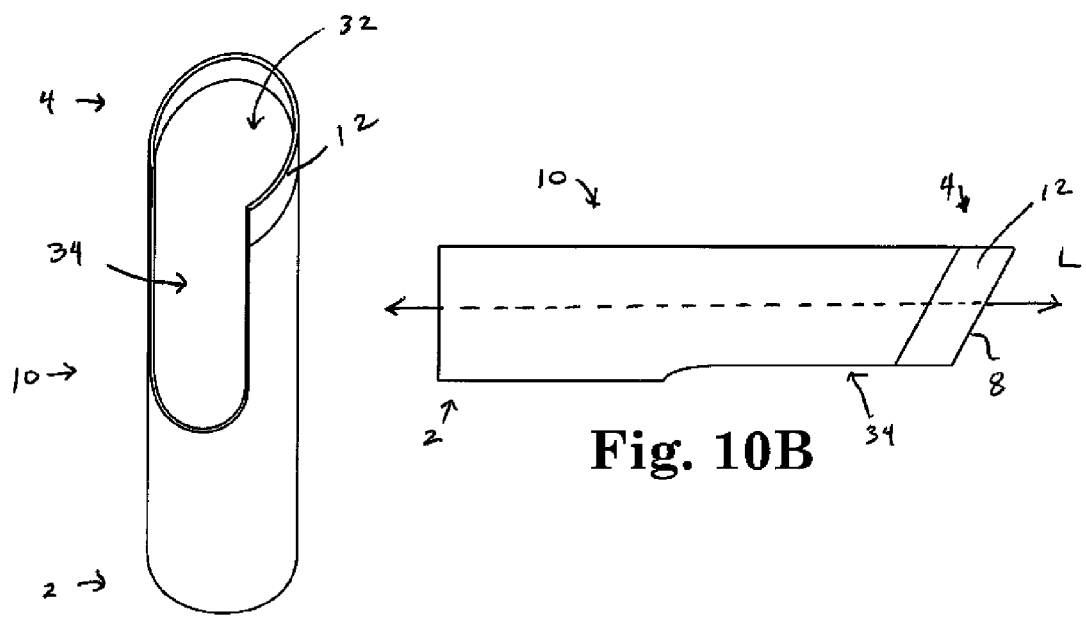
Fig. 10A
Fig. 10B

SYSTEMS, TOOLS, AND METHODS FOR TREATMENTS OF PELVIC CONDITIONS

PRIORITY CLAIM

This application claims the benefit from International No. PCT/US2011/053985, which was granted an International Filing date of Sep. 29, 2011, which in turn claims priority under 35 USC § 119(e) from United States Provisional Patent Application having U.S. Ser. No. 61/502,694, filed Jun. 29, 2011, entitled "SYSTEMS, IMPLANTS, TOOLS, AND METHODS FOR TREATMENTS OF PELVIC CONDITIONS," U.S. Ser. No. 61/387,751, filed Sep. 29, 2010, entitled "SYSTEMS, IMPLANTS, TOOLS, AND METHODS FOR TREATMENTS OF PELVIC CONDITIONS," U.S. Ser. No. 61/515,685, filed Aug. 5, 2011, entitled "SYSTEMS, IMPLANTS, TOOLS, AND METHODS FOR TREATMENT OF PELVIC CONDITIONS" and U.S. Ser. No. 61/515,638, filed Aug. 5, 2011, entitled "TOOLS AND METHODS FOR TREATMENT OF PELVIC CONDITIONS,", which applications are incorporated herein by reference in their entireties.

FIELD OF THE INVENTION

The invention relates generally to systems, tools, and related methods for treating pelvic conditions including but not limited to prolapse conditions, for example by transvaginal sacral colpopexy procedures.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed. Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina. Vaginal vault prolapse and enterocele represent challenging forms of pelvic disorders for surgeons. These procedures often involve lengthy surgical procedure times. Abdominal sacralcolpopexy (SCP) is considered to be an especially efficacious treatment, but it can be complicated and is generally considered invasive.

SUMMARY

Devices, systems, and methods as described can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies and the like.

Certain described embodiments of devices and methods involve the use of a retractor or "expansion member" adapted to provide port access and guidance to a surgical site. These embodiments involve placement of an elongate expansion member through a body orifice or incision and to a surgical site, to create an access space from the exterior of the patient to the surgical site. The expansion member is useful to retract tissue, create an access space, and allow surgical instruments such as sharp tools to safely access the surgical site. Certain of these described embodiments relate generally to various means, devices, and techniques for providing a clear view of a surgical site in a region of a sacrum, and nearby anatomy, through a vaginal incision. In several examples, this is provided by way of a device that can be inserted into a vaginal incision and then used to expand or dilate tissue.

In described examples, desired retraction functionality is provided by a device that can be changed in its size or shape, to contact and then move, expand, or dilate (e.g., retract) tissue. An expansion member may include two or more pieces (e.g., longitudinal panels or blades) that are optionally hinged or slidably connectable and able to move laterally or longitudinally relative to each other. The pieces can be moveable relative to each other in a manner that allows the pieces to define a space (access space) therebetween, the space being capable of being varied in size, e.g., "expandable." In specific embodiments, the device can be inserted into a vaginal incision and then expanded, dilated, manipulated, or otherwise used for tissue retraction to create a working space between the vaginal introitus and the vaginal apex, a posterior location of a pelvic region, or a region of sacral anatomy. Certain preferred versions of these tools can include distal end functionality to add efficiency to a surgical procedure, e.g., for performing a transvaginal sacral colpopexy, such as a lighting feature, an anchor driving feature, an optical feature that allows viewing of the surgical site, suction, irrigation, or a dissection device.

In one aspect, the invention relates to an expansion member that includes a proximal end, a distal end, a length from the proximal end to the distal end, and an opening on a side of the expansion member along a distal portion of the length, not extending the entire length. The distal end is capable of being placed through a vaginal introitus to provide access to a region of sacral anatomy.

In another aspect the invention relates to an expansion member that includes a proximal end, a distal end, and a length extending from the proximal end to the distal end, and two longitudinal panels extending in the length direction. The panels are connected by a longitudinal hinge and one of the two longitudinal panels is moveable (e.g., rotatable) about the other panel at the hinge. The expansion member is capable of exhibiting an open configuration with the panels spaced apart to create a space between the panels, and a closed configuration with the panels relatively closer together.

In another aspect, the invention relates to methods of transvaginally performing pelvic surgery to support a vaginal apex. The methods include: providing an expansion member as described herein, inserting the distal end through a vagina introitus, and using the expansion member to provide access to a region of sacral anatomy.

See also Applicant's co-pending PCT patent application number PCT/US2011/053938, entitled "SYSTEMS, TOOLS, AND METHODS FOR TREATMENTS OF PEL- VIC CONDITIONS," filed on Sep. 29, 2011, the entirety of which is incorporated herein by reference.

BRIEF DESCRIPTION OF THE DRAWINGS

FIGS. 5C, 5D, and 5E are end views of an embodiment of an expansion member.

FIGS. 9A and 9B are top perspective and side views of an embodiment of an expansion member.

FIGS. 10A and 10B are top perspective and side views of an embodiment of an expansion member.

DETAILED DESCRIPTION

Figure 1A:
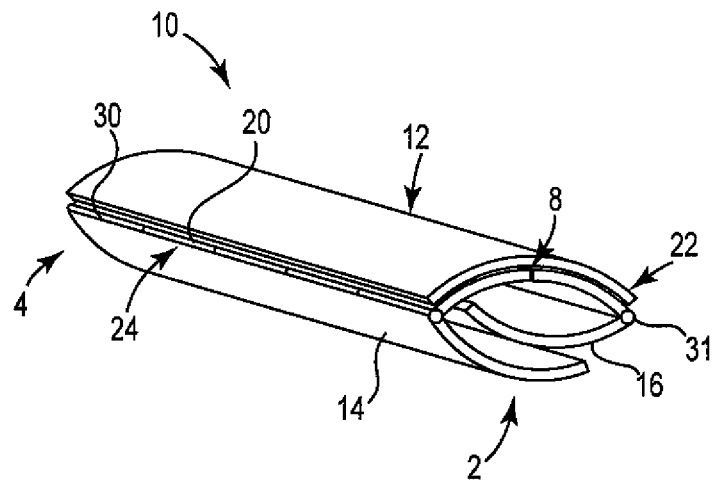
FIGS. 1A and 1B are end perspective views of an embodiment of an expansion member.

Pelvic disorders include cystocele, rectocele, enterocele, and uterine and vaginal vault prolapse, urinary and anal incontinence, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to a configuration outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures are surgical methods that place a sling to stabilize or support the bladder neck or urethra. They are typically used to treat incontinence. There are a variety of different sling procedures. Slings used for pubovaginal procedures differ in the type of materials, size and shape, anchoring methods, and anchor placement. Examples of sling procedures are disclosed in U.S. Pat. Nos. 5,112,344; 5,611,515; 5,842,478; 5,860,425; 5,899,909; 6,039,686, 6,042,534 and 6,110,101.

A sacral colpopexy is a procedure for providing vaginal vault suspension. It may be performed through an abdominal incision, a vaginal incision, or laparoscopically. Typically, this procedure is accompanied by an abdominal enterocele repair and cul-de-sac obliteration. A sacral colpopexy entails suspension (by use of an implant such as a strip of mesh) of the vaginal cuff to a region of sacral anatomy such as the sacrum (bone itself), a nearby sacrospinous ligament, uterosacral ligament, or anterior longitudinal ligament at the sacral promontory. An implant such as a synthetic mesh can be carefully customized or assembled into a special shape by the surgeon. According to some procedures, a surgeon manually cuts a sheet of the mesh and stitches elements of the mesh to form the special shape. The literature reports surgeons suturing mesh material into various T-shaped articles. See Winters et al., "Abdominal Sacral Colpopexy and Abdominal Enterocele Repair in the Management of Vaginal Vault Prolapse," Urology 56 (Suppl 6A) (2000): 55-63; and Paraiso et al, "Laparoscopic Surgery for Enterocele, Vaginal Apex Prolapse and Rectocele," Int Urogynecol J (1999).

In some sacral colpopexy (SCP) procedures that also involve a hysterectomy, an implant can attach to posterior vaginal tissue remaining after removal of the uterus and cervix, and also to anatomy to support the vaginal tissue at or around the sacrum such as to uterosacral ligaments, the sacrum itself, a sacrospinous ligament, or anterior longitudinal ligament at the sacral promontory (i.e., to a component of the sacral anatomy).

As used herein, the term "anchor" refers non-specifically to any structure that can connect an implant to tissue of a pelvic region. The tissue may be bone or a soft tissue such as a muscle, fascia, ligament, tendon, or the like. The anchor may be any known or future-developed structure useful to connect an implant to such tissue, including but not limited to a clamp; a suture; a soft tissue anchor such as a self-fixating tip; a bone anchor; a screw, spiral, helical anchor, or coil; or any structure useful to connect an implant to soft tissue or bone of a pelvic region.

Embodiments of expansion members can include multiple elongate panels (portions, pieces, sections, segments, or the like) that extend longitudinally from a proximal end of each panel to a distal end of each panel, also between a proximal end of the expansion member and a distal end of the expansion member. The panels meet and are optionally connected or connectable along longitudinal edges that allow relative movement of the two panels about the longitudinal connection, i.e., longitudinally. A longitudinal connection along edges of two different panels can include a longitudinal hinge to allow movement of one panel laterally, e.g., by pivoting about the longitudinal hinge. Alternately or in addition, a longitudinal connection along edges of two adjacent panels can include a sliding engagement that allows an edge of one panel to slide longitudinally along an edge of an adjacent panels.

A panel is a generally elongate, substantially rigid member that makes up a structural piece of the expansion member. Alternate terms may include a "piece," "section," "segment," or "blade" constituent of an expansion member. A panel can be substantially flat or can exhibit a curved cross-sectional profile. One or more longitudinal edges can be straight or curved, extending longitudinally between a proximal end and a distal end of each panel. A panel can be made of a substantially rigid material such as a plastic or other polymer, metal, or other material useful for a surgical tool or device. The length of each panel can be as desired for an expected application of the expansion member. For certain embodiments of expansion members, a length of a panel can be sufficient to extend between a space exterior to a vaginal introitus and a region of sacral anatomy, when placed transvaginally. A width of a panel can be sufficient to create an access space between multiple panels of an expansion member as described herein, and can depend on the number of separate longitudinal panels that are used to construct an expansion member, e.g., two, three, four, or more. A panel may generally have a length that is greater in dimension that a width, and have a thickness dimension that is a fraction of an inch, e.g., 1 to 3 millimeters.

A panel includes a longitudinal edge that connects at a hinge to a longitudinal edge of another panel, along a straight or a curved hinge connection, to allow the panels to rotate relative to each other by pivoting about the hinge connecting the longitudinal edges. A "hinge" can be a mechanical connection between two panels that connects the two panels and allow the panels to move (rotate) relative to each other by pivoting about the hinge, at a fixed axis of rotation. An example of a useful type of hinge is a hinge made of a flexible material connecting one edge of a panel to an edge of an adjacent panel, the flexible material being sufficiently flexible to allow the two panels to rotate or pivot relative to the flexible material and the connected edges. This type of hinge may sometimes be referred to as a "living hinge," a "flexible connective hinge," or a "connective membrane." Examples of flexible materials that may be useful as a hinge material include polymeric materials such as natural rubber, synthetic rubber, silicon rubber, polyurethane, polyolefin, and the like. Another example of a useful type of hinge is a hinge that includes a mechanical linkage between edges of adjacent panels. A mechanical linkage can include one or a series of multiple (e.g., alternating) bearings (e.g., pins or a single rod) and loops (cylinders or other moveable fittings). For example, a bearing (e.g., multiple pins attached to one or both edges of the panels, or a single rod extending between the panels) can be rotatably connected to one or multiple alternating loops or cylinders connected at edges of the panels. Examples of hinges of these types include hinges sometimes referred to as a barrel hinge, a piano hinge, and a flag hinge.

The expansion member includes at least two panels, optionally three, four, or even more panels, with each panel connected to or connectable to at least one adjacent panel, along a hinge, to connect a longitudinal edge of one panel to a longitudinal edge of the adjacent panel.

Each longitudinal edge may be straight, or curved. For example, a curved edge may be used in combination with a living hinge. When a curved edge is used in combination with a living hinge (to produce a curved hinge), one or two connected panels of the expansion member connected along the curved hinge may exhibit a shape-changing feature. The panels may be flat when the expansion member is in a closed configuration, and will take on a curved profile upon the expansion member being opened.

The panels can open and close relative to each other to alternate between an open configuration and a closed configuration. The panels may optionally be connected to handles at the proximal end, which can be used to move (e.g., open and close) the panels.

Each panel may exhibit a flat cross section, or a curved cross section such that a cross sectional space defined between opposing or adjacent panels of an expansion member (an access space) includes a circular, semi-circular, or a segment or multiple cross-sectional semi- or partial-circular portions.

Optionally, an opening (e.g., slot or channel) may extend along an inferior (bottom) side of an expansion member. An opening may extend from the distal end, toward the proximal end, partially along the length of the expansion member. Alternately, an opening can extend the entire length between the distal end and the proximal end. The opening can allow desired access to tissue at a distal end of the expansion member during a surgical procedure. The expansion member may not fully enclose an access space along the length or around a circumference of the device, between the distal and proximal ends, but may leave one portion or side (along the partial or total length of the expansion member) open, giving access to tissue. For example, a "bottom" side of an expansion member may lack structure, leaving an opening along a length of the device to allow access to a peritoneum and fixation of mesh at locations of exposed tissue, e.g., by suturing.

Other features can include a taper (e.g., a narrowing of the shape from the proximal end to the distal end; ribs for retention within the patient; sacral mating geometry (shaping of the distal end) or materials (e.g., conforming materials such as "tissue wipers") at the far end or tips of one or more segments of a tool; a longitudinal (parallel or approximately parallel to a longitudinal axis or longitudinal dimension of the expansion member) (straight or curved) hinge between moveable segments; selective expansion (adjustment of a width dimension) of an expansion member at different locations along a length of an expansion member, e.g., to match the anatomy of a patient; selective adjustment of a length dimension of an expansion member, e.g., to match the anatomy of a patient; and locks or ratchets to maintain one or more selectively set dimensions of an expansion member.

Also optionally, an expansion member can include a locking mechanism that will hold the panels in the open configuration while the expansion member is located within a patient, to cause the expansion member to remain open and expand tissue to create the access space.

An expansion member can be used to allow surgical items such as tools, sutures, implants, or components thereof, or other objects (e.g., sharp objects) to be passed safely through an access space of the expansion member from an external location to an internal surgical site.

In certain embodiments an expansion member can be useful for transvaginally accessing a female pelvic anatomy, especially a female pelvic anatomy, to access tissue of the posterior pelvic region such as to perform a transvaginal sacral colpopexy (TSCP) procedure. An expansion member can have a length to allow such access when the expansion member is placed transvaginally, e.g., a length to allow a distal end of the expansion member to access pelvic tissue while a proximal end of the expansion member extends through a vaginal opening to a location external to the patient. The proximal end of the expansion member remains external to the patient during use to allow a surgeon or other user to access and manipulate the proximal end and access a surgical site at the distal end, through the access space of the expansion member. Exemplary lengths between a proximal end of an expansion member and a distal end of the expansion member may be in the range from 13 to 18 centimeters, especially for use in a female patient to transvaginally access a posterior location of a pelvic region such as a region of sacral anatomy.

The diameter of the expansion member (defining the access space) can be useful to allow the tool to be inserted and placed in a patient (e.g., transvaginally) with reduced trauma. Optionally, as described elsewhere herein, a diameter of the expansion member, or the size of the access space, can be variable, such as by being expandable after placement within a patient, to allow increased and expanded access to tissue at a surgical site.

An expansion member can include one or more functional features within the access space or at the distal end (or distal region) such as one or more of a dissection feature (a mechanical dissection using a sharp blade, or hydrodissection), a blunt dissection feature, a viewing (visualization) feature, a feature for illumination of a surgical location, a feature for fluid delivery at a surgical location, a feature for irrigation at a surgical location, a feature for suction at a surgical location, and a feature for placing anchors (bone anchors, soft tissue anchors such as a self-fixating tip, sutures, etc.) into a desired target tissue at a surgical location such as a coil driver. An expansion member may include an optional laser at the proximal end that can shine along the centerline of the expansion member, within the access space.

An expansion member or portion or component thereof can be constructed of any known or compatible materials, including polymers or metals. A panel, handle, mechanical hinge component, or other rigid structure can be constructed of metal or a rigid polymeric material such as a polypropylene, polyacrylate, polycarbonate, stainless steel, steel, polyester, or other similar materials. A non-rigid material such as a living hinge or a conformable distal end can be made of a non-rigid, flexible, pliable material suitable for use in a surgical instrument, such as a flexible, pliable polymer. Examples include natural or synthetic rubber, silicone, polyurethane, polyolefin (e.g., polypropylene, polyethylene), and the like.

Referring to FIGS. 1A, 1B, 1C, and 1D, retractor or expansion member 10, including proximal end 2, distal end 4, and three longitudinal panels, 12, 14, and 16, is configured for use during a surgical procedure to provide access to a surgical site or anatomy, e.g. transvaginal access to a region of sacral anatomy. Panel 12 is a center panel having edges 20 and 22. Optionally and as illustrated, center panel 12 is capable of expanding laterally along expandable joint 8, which is an expandable joint running along a length of panel 12 between proximal end 2 and distal end 4. Panel 14 is a side panel having edge 24. Panel 16 is a side panel having edge 26. Edges 20 and 24 meet along longitudinal hinge 30. Edges 22 and 26 meet along longitudinal hinge 31. Each of hinges 30 and 31 may be any type of hinge such as a living hinge (e.g., a flexible polymeric membrane, film, or other connection) or a mechanical hinge, and can optionally be a locking hinge that is capable of being secured (e.g., "locked") in an open configuration during use expanding tissue, and subsequently unlocked to allow the panels to be folded into a closed configuration (for insertion into and removal from a patient). In the open configuration, longitudinal opening (e.g., slot or channel) 34 extends along the bottom length of expansion member 10, from proximal end 2 to distal end 4.

Figure 1B:
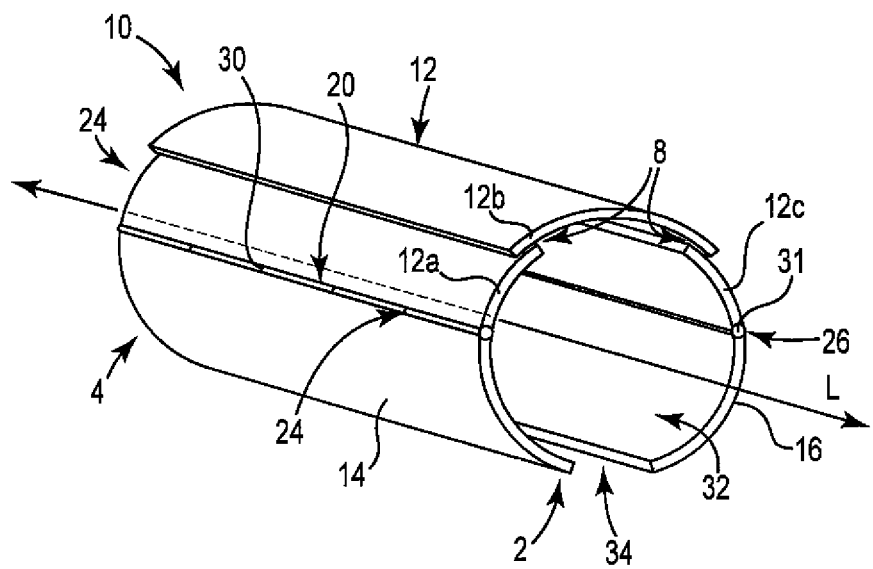

In a closed configuration as illustrated at FIG. 1A, hinges 30 and 31 are closed and side panels 14 and 16 are folded against (and below, or inferior to) center panel 12. Center panel 12 (at expandable joint 8) is in a closed or non-expanded configuration. From that closed configuration, side panels 14 and 16 can be moved by rotating panels 14 and 16 about hinges 30 and 31 (see arrows at FIG. 1C), respectively. In the open configuration as illustrated at FIG. 1B, hinges 30 and 31 are opened and side panels 14 and 16 are spread laterally; access space 32 is the longitudinal interior space between opened panels 12, 14, and 16, including longitudinal axis "L."

Figure 1C:
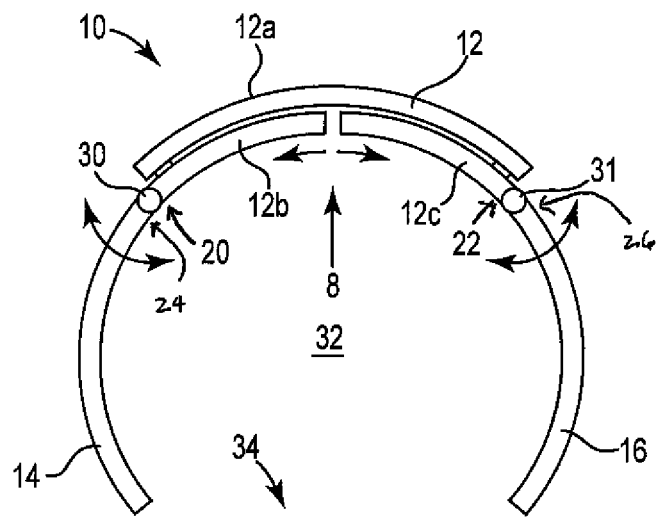
FIGS. 1C and 1D are end views of an embodiment of an expansion member.
Figure 1D:
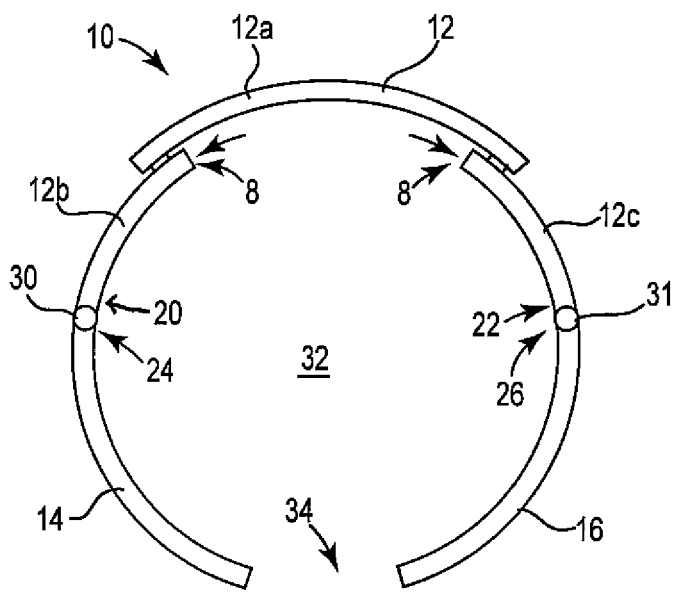

Center panel 12 includes longitudinal leafs or segments 12a, 12b, and 12c connected at longitudinal expandable joint 8. Center panel 12 can be expanded laterally along expandable joint 8 from a closed or non-expanded configuration (see FIG. 1C) by lateral movement of leafs 12a and 12c, relative to leaf 12b, as indicated by the arrows shown at FIGS. 1C and 1D. Expandable joint 8 can be of any structure allowing lateral movement between the leafs as described, such as lateral sliding rails (not shown) that allow connected or independent movement of each panel 12a and 12c, relative to 12b. In one embodiment, leafs 12a and 12c can optionally be connected to side panels 14 and 16 so that movement (unfolding) of side panels 14 and 16 causes movement (expansion) of leafs 12a and 12c relative to 12b. Accordingly, opening or spreading side panels 14 and 16 will also expand center panel 12 along expandable joint 8, such as along lateral slider rails. FIG. 1C shows expansion member 10 with side panels 12 and 14 in an unfolded (open) configuration, and center panel 12 (and leafs 12a, 12b, and 12c) in a non-expanded configuration. FIG. 1D shows expansion member 10 with side panels 12 and 14 in an unfolded (open) configuration, and center panel 12 in an expanded configuration, with leafs 12a and 12c slid laterally to open or widen along expandable joint 8.

In use, expansion member 10 can be placed in the closed or folded configuration by folding side panels 14 and 16 against the underside of center panel 12 and placing expandable joint 8 in the non-expanded (closed) configuration. In the closed configuration, expansion member 10 has a reduced cross-sectional profile that facilitates introduction of the expansion member through an incision or body orifice (e.g., into a vaginal introitus and optionally through an incision at a posterior of vaginal tissue). Upon placement into a body orifice or incision, expansion member 10 can be converted to an open configuration by unfolding side panels 14 and 16 away from center panel 12 and by optionally expanding center panel 12 along optional expanding hinge 8. Side panels 14 and 16 rotate about hinges 30 and 31 (see arrows at FIG. 1C), expanding the expansion member structure laterally and creating access space 32 between panels 12, 14, and 16. The unfolded device retracts tissue by pushing tissue away from longitudinal axis L, laterally, due to the movement of side panels 14 and 16 away from longitudinal axis L. The opened expansion member includes access space 32, which is the space located inside of and between panels 12, 14, and 16, between proximal end 2 and distal end 4, and including longitudinal axis L. Expansion member 10 can optionally be expanded farther by expanding center panel 12 laterally at expanding hinge 8, thus increasing the size of access space 32.

For use in a transvaginal procedure to access tissue in a region of a sacrum, a surgeon is able to insert expansion member 10 transvaginally, when expansion member 10 is in the closed configuration. Proximal end 2 remains external to the patient, and distal end 4 passes transvaginally to a location at a posterior pelvic region, e.g., at a surgical location of a region of sacral anatomy. During or after insertion, expansion member 10 can be opened by unfolding side panels 14 and 16 to create access space 32 extending from proximal end 2 to distal end 4. Center panel 12 can be expanded laterally. Optionally and preferably expansion member 10 (e.g., side panels 14 and 16, and expanded center panel 12) can be locked into the open (expanded) configuration, and a surgical procedure (e.g., a transvaginal sacralcolpopexy) can be performed. After the surgical procedure is completed, expansion member 10 can be optionally unlocked, folded, and removed from the patient.

Referring to FIGS. 2A, 2B, 2C, 2D, and 2E, retractor or expansion member 50 includes proximal end 52, distal end 54, and four longitudinal panels, 62, 64, 66, and 68. Expansion member 50 is configured for use during a surgical procedure to provide access to a surgical site or anatomy, e.g. transvaginal access to a region of sacral anatomy. Panel 62 is an upper center panel (or top panel) having edges 80 and 82 extending longitudinally between proximal end 52 and 54. Panel 64 is a side panel having upper edge 84 and lower edge 86, each extending longitudinally between proximal end 52 and 54. Panel 66 is a side panel having upper edge 76 and lower edge 78, each extending longitudinally between proximal end 52 and 54. Edges 82 and 84 meet along longitudinal hinge 56. Edges 82 and 84 meet along longitudinal hinge 58. Each of hinges 56 and 58 may be any type of hinge such as a living hinge, and as illustrated are flexible polymeric membranes sometimes referred to as a living hinge.

Figure 2A:
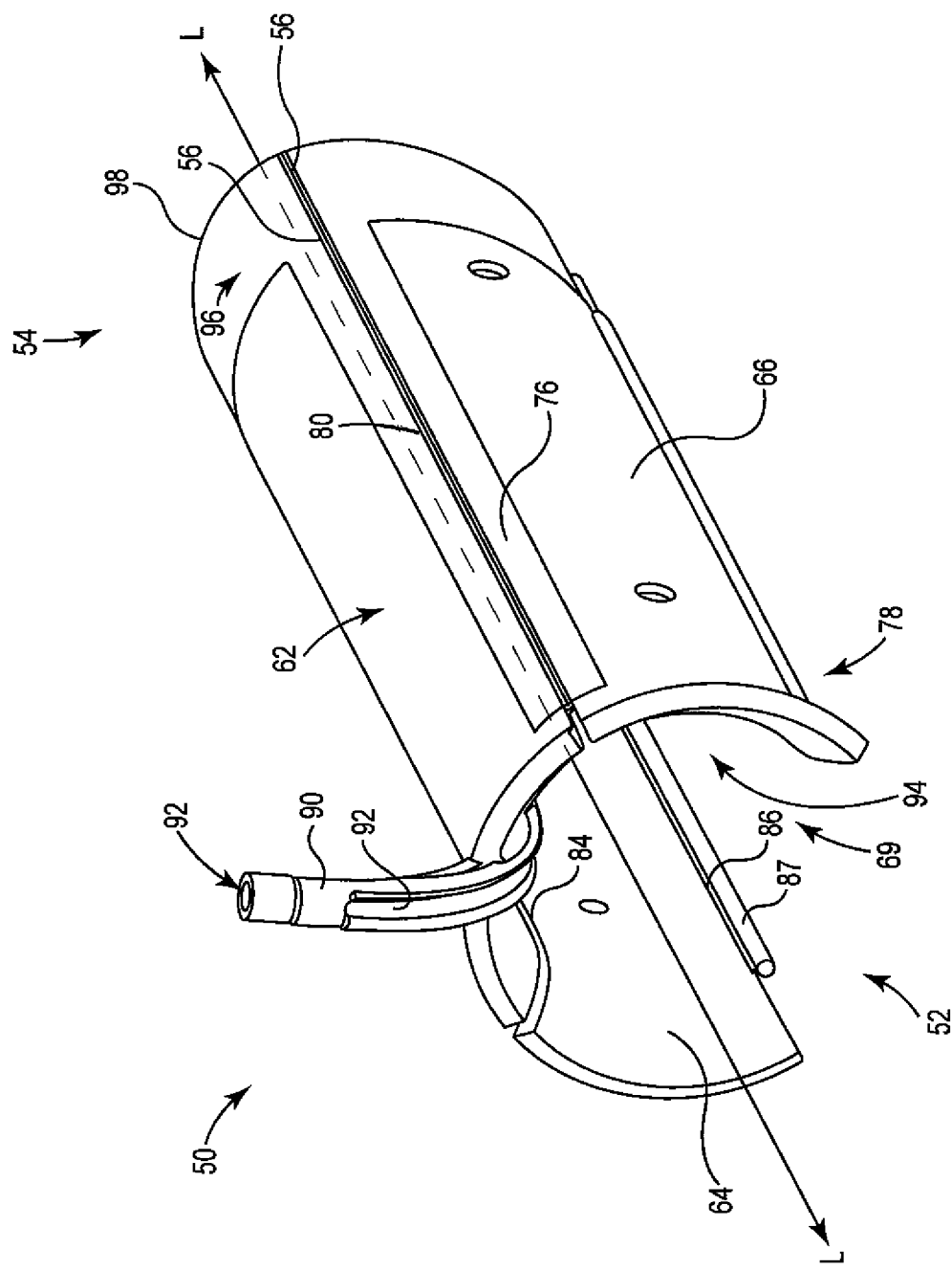
FIGS. 2A and 2B are end perspective views of an embodiment of an expansion member.
Figure 2B:
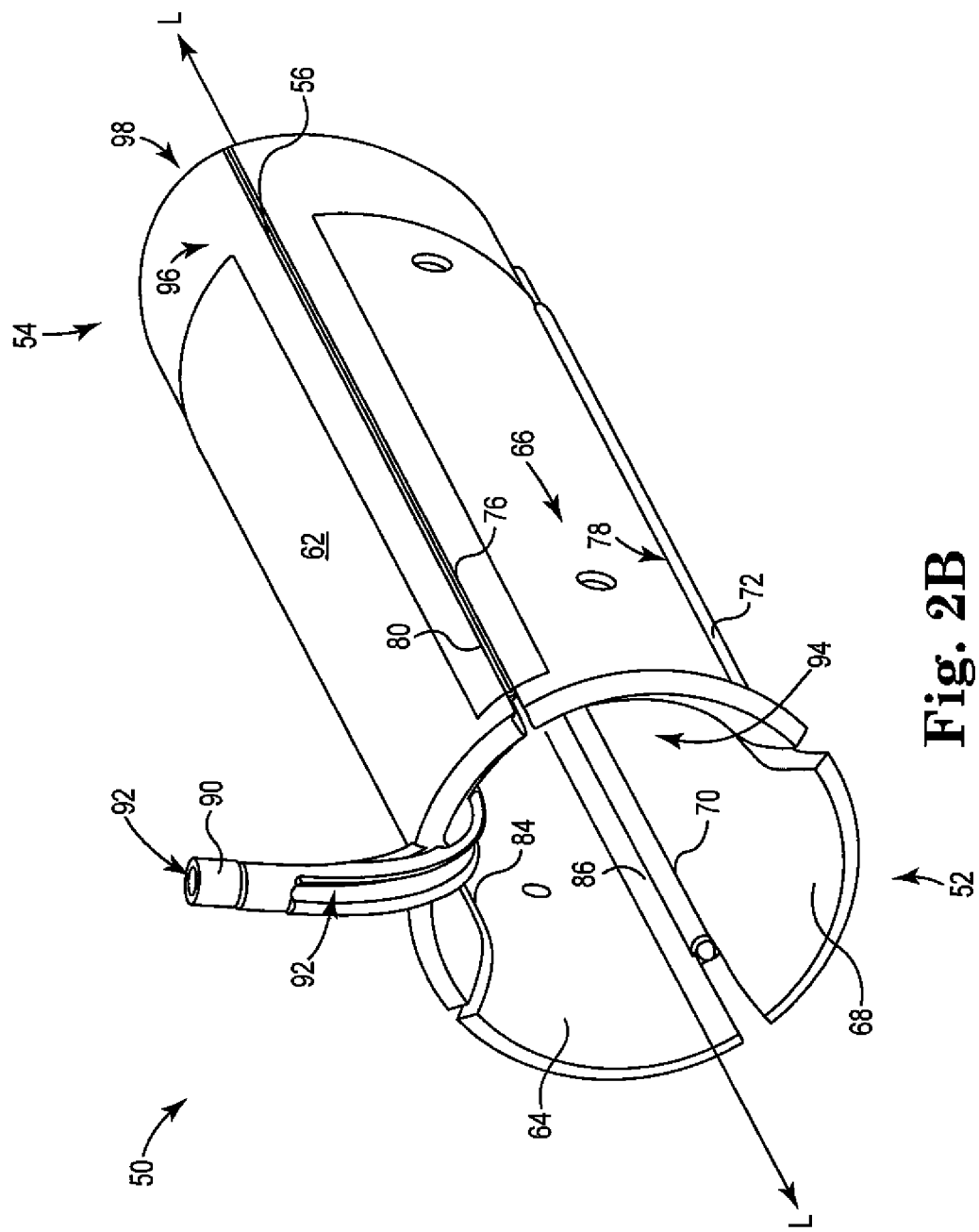
Figure 2C:
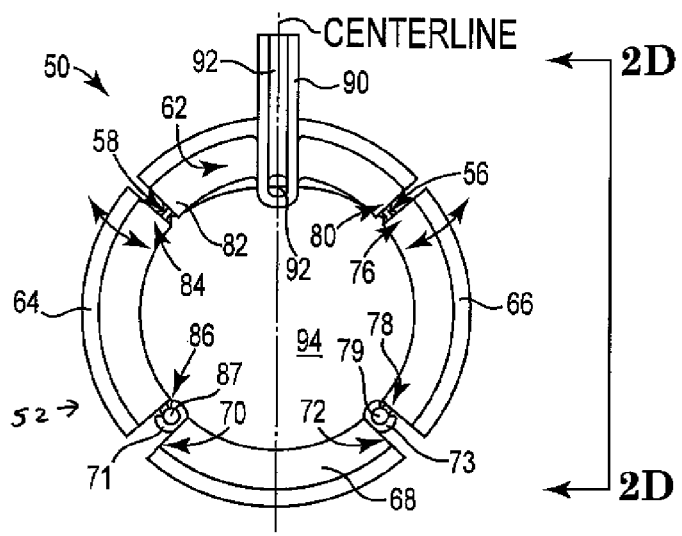
FIG. 2C is an end view of an embodiment of an expansion member.
Figure 2D:
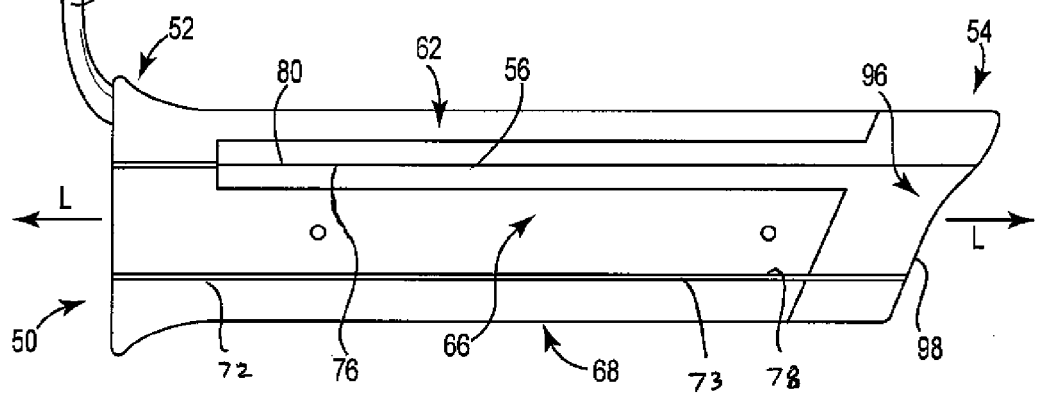
FIG. 2D is a side view of an embodiment of an expansion member.
Figure 2E:
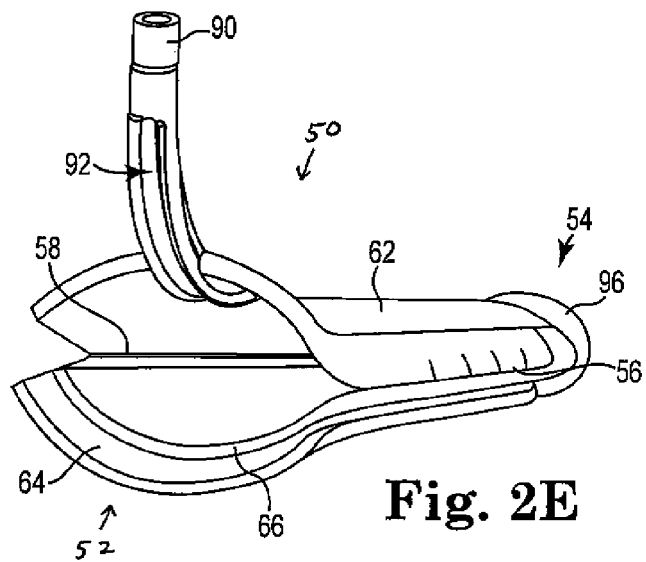
FIG. 2E is an end perspective view of an embodiment of an expansion member.

Panels 62, 64, and 66 can be configured in either an open or a closed configuration. In a closed configuration, as illustrated at FIG. 2E, hinges 56 and 58 are closed and side panels 66 and 64 (respectively) are folded against (and below, or inferior to) upper center panel 52. From that closed configuration, side panels 64 and 66 can be moved by rotating panels 64 and 66 about hinges 58 and 56 (see arrows at FIG. 2C), respectively, resulting in an open configuration as illustrated at FIGS. 2A, 2B, 2C, and 2D. In the open configuration, hinges 58 and 56 are opened and side panels 66 and 64 are spread laterally; access space 94 is the longitudinal interior space between opened panels 62, 64, and 66, including longitudinal axis "L."

When panels 62, 64, and 66 are in the open configuration, lower center panel (or bottom panel) 68 can be inserted into the longitudinal opening (e.g., slot or channel) 69 located between lower edges 86 and 78. See FIGS. 2B, 2C, and 2D, showing expansion member 50 assembled in the open configuration, with lower center panel 68 installed. As shown in detail at FIG. 2C, lower center panel 68 includes edges 70 and 72 extending longitudinally, and can slidably engage lower edges 86 and 78 of side panels 64 and 66. The adjacent edges of lower center panel 68 and each of the side panels (at their lower edges) can be connected by a desired sliding connection, such as opposing channel and beam structures, or any useful or equivalent set of opposing sliding engagements.

FIG. 2C shows an exemplary sliding engagement between adjacent edges of lower center panel 68 and side panels 64 and 66. As illustrated, each of edges 78 and 86 includes an elongate, bead (79 and 87) having a round or circular cross-section (alternately a bar, rod, rider, ball, insert, or beam, optionally of a round, circular, or non-circular, optionally cornered cross-section) connected to or formed in or along each edge. Each of edges 70 and 72 includes an elongate, longitudinal channel (71 and 73) (alternately an opening, groove, depression, hollow, dip, indent, holder, or conduit) connected to or formed in or along the edge. Each channel (71, 73) is capable of slidably receiving a bead (79, 87), to slidably (and reversibly) connect the two opposing edges (70, 72) of lower center panel 68, to an adjacent lower edge (86, 78) of side panels (64, 66).

Still referring to FIGS. 2A through 2E, expansion member 50 is shown to include optional optical fiber holder 90 and channel 92. Channel 92 extends from holder 90 at proximal end 52 in a distal direction along upper center panel 62 to a location about midway between proximal end 52 and distal end 54. Holder 90 and channel 92 allow for an optical fiber (not shown) to be inserted at proximal end 52, passed through channel 92 in a distal direction along a length of expansion member 50 for placement of the optical fiber to provide light to access space 94, to receive images from access space 94, or both.

Also illustrated as an optional feature of an expansion member, distal end 54 includes distal edge 98 that is situated at an angle relative to longitudinal axis L, when expansion member 50 is viewed from a side (see FIG. 2D). As illustrated, distal edge 98 is angled or slanted relative to longitudinal axis L in a direction that allows edge 98 to align with a slant of pelvic anatomy at a posterior region of a patient's pelvis, such as at a region of sacral anatomy, while expansion member 50 is installed transvaginally. To achieve this angle, a length between the proximal and distal ends of the expansion member is longer at the top of the expansion member and is relatively shorter at the bottom of the expansion member (when viewed from a side). Referring to exemplary expansion member 50, the (centerline) length (see FIG. 2C) of top center panel 62 is greater than the (centerline) length of bottom center panel 68. The length of the upper center panel and side panels measured at locations that extend between these upper (centerline) and lower (centerline) locations can gradually change between the top (centerline) length and the bottom (centerline) length.

Also illustrated is another optional feature of an expansion member, a distal edge 98 that comprises or is composed of a flexible material. Extension 96, which includes distal edge 98, is made of a flexible, conformable material that is capable of changing shape and conforming to anatomical tissue such as muscle, bone, or ligaments located at a posterior pelvic region. The flexible, conformable material may be the same as or different than the material used to produce a living hinge, e.g., a non-rigid polymer or foam (open or closed cell) material comprising one or a combination of natural rubber, synthetic rubber, silicone, polyurethane, polyolefin, and the like.

In use, expansion member 50 can be placed in the closed or folded configuration by folding side panels 64 and 66 against the underside of center panel 62 (see FIG. 2E). In the closed configuration, the expansion member can be inserted through an incision or body orifice (e.g., into a vaginal introitus and optionally through a transvaginal incision at a posterior of vaginal tissue). Upon placement into a body orifice, expansion member 50 can be converted to an open configuration by unfolding side panels 64 and 66 away from center panel 62 (see arrows at FIG. 2C). Side panels 64 and 66 rotate about hinges 58 and 56, expanding the expansion member structure laterally and creating access space 94. The unfolded device retracts tissue by pushing tissue away from longitudinal axis L laterally due to the movement of side panels 64 and 66 away from longitudinal axis L. The opened expansion member includes access space 94, which is the space located inside of and between panels 62, 64, and 66, between proximal end 52 and distal end 54, and including longitudinal axis L. After placing and opening panels 62, 64, and 66 as desired, lower center panel 68 can be inserted by sliding between lower side panel edge 86 and lower side panel edge 78, with edge 70 of lower center panel 68 slidably engaging lower edge 86 of side panel 64, and with edge 72 of lower center panel 68 slidably engaging lower edge 78 of side panel 66. Proximal end 52 remains external to the patient, and distal end 54 passes transvaginally to a location at a posterior pelvic region, e.g., placing distal edge 98 in contact with tissue of a region of sacral anatomy. During or after insertion, expansion member 50 can be opened by unfolding, and lower center panel 68 can be installed by sliding between the lower edges of the side panels. After the surgical procedure is completed, lower center panel 68 can be slid out of the patient and removed from between the lower edges of the side panels and expansion member 50 can be folded, and removed from the patient.

Figure 3A:
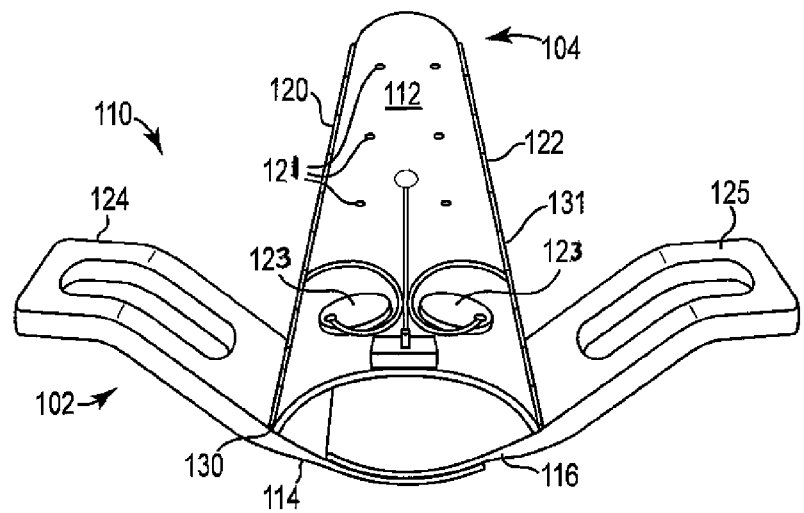
FIGS. 3A and 3B are top perspective views of an embodiment of an expansion member.
Figure 3B:
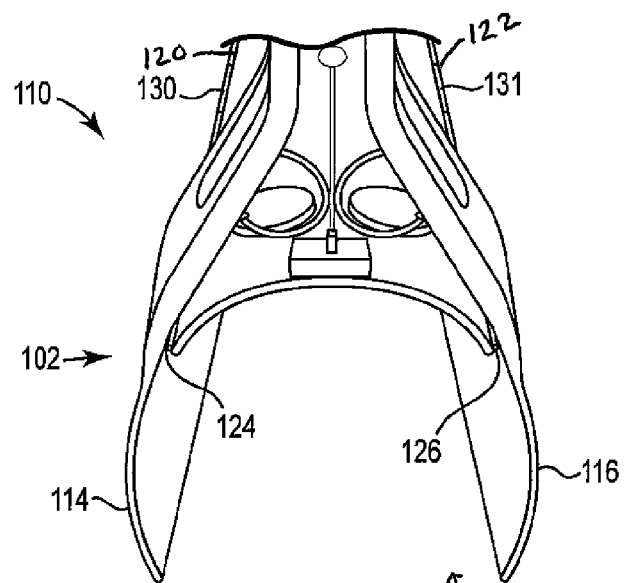
Figure 3C:
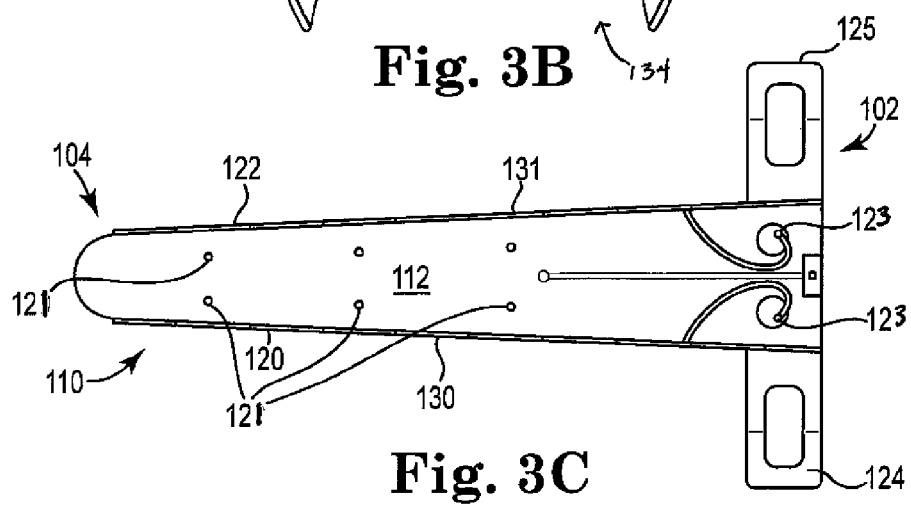
FIG. 3C is a top view of an embodiment of an expansion member.
Figure 4A:
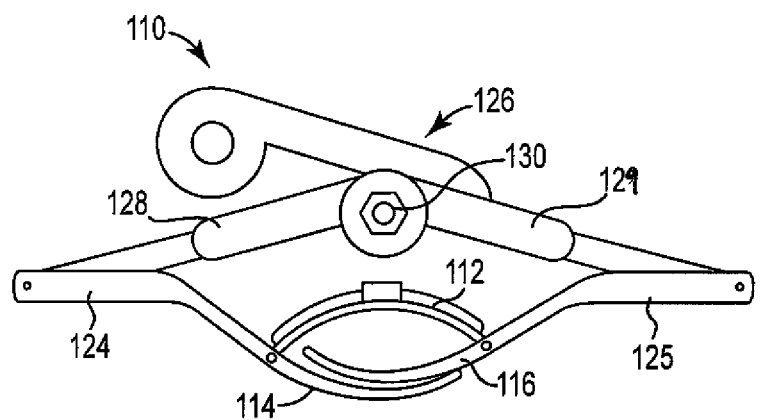
FIGS. 4A and 4B are end views of an embodiment of an expansion member.
Figure 4B:
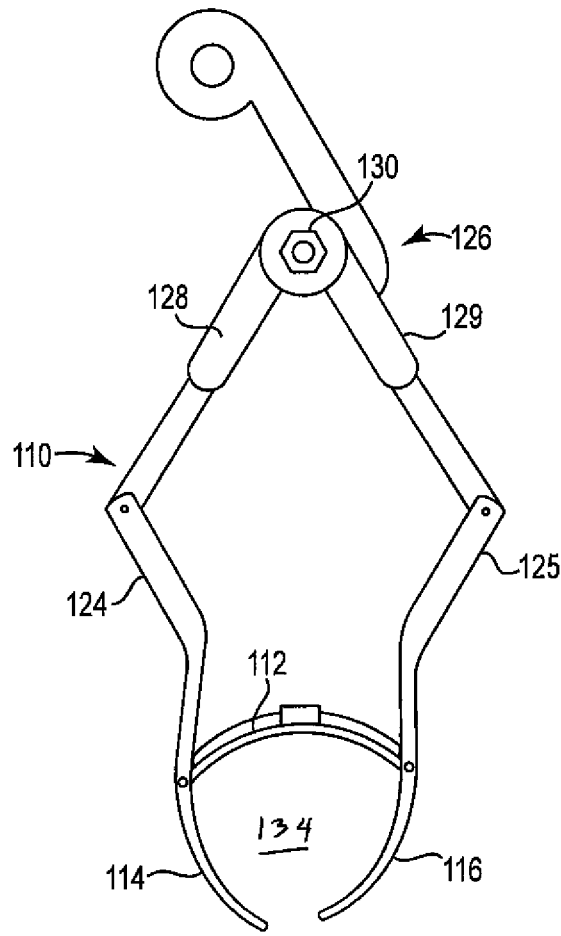
Figure 4C:
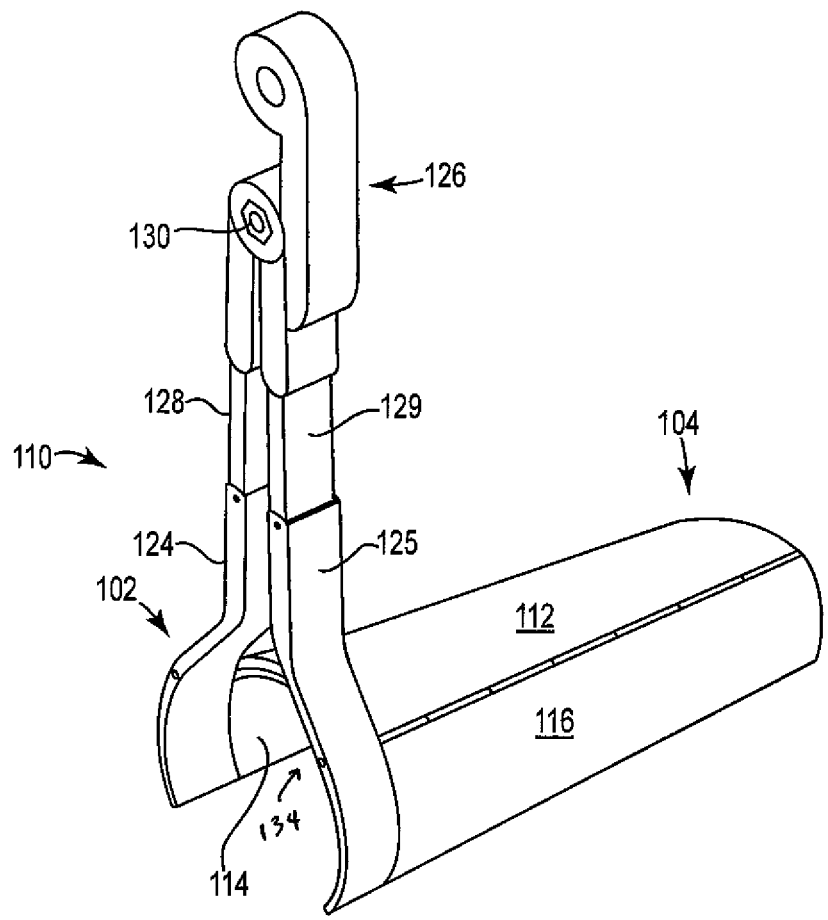
FIG. 4C is a side perspective view of an embodiment of an expansion member.
Figure 4D:
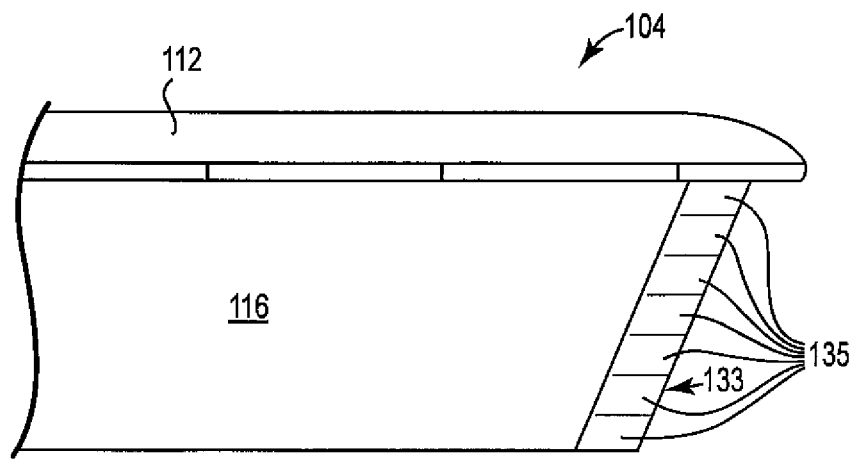
FIG. 4D a side view of an embodiment of a distal end of an expansion member.

Referring to FIGS. 3A, 3B, and 3C, retractor or expansion member 110 includes proximal end 102, distal end 104, and three longitudinal panels, 112, 114, and 116. Expansion member 110 is configured for use during a surgical procedure to provide access to a surgical site or anatomy, e.g. transvaginal access to a region of sacral anatomy. Panel 112 is a center panel having edges 120 and 122. Panel 114 is a side panel having edge 124. Panel 116 is a side panel having edge 126. Edges 120 and 124 meet along longitudinal hinge 130. Edges 122 and 126 meet along longitudinal hinge 131. Each of hinges 130 and 131 may be any type of hinge such as a living hinge or a mechanical hinge. Expansion member 110 can preferably be capable of securely unfolding into an open (e.g., locked) configuration during use and maintaining that position during use, and subsequently being folded into a closed configuration. In the open configuration, longitudinal opening (e.g., slot or channel) 134 extends along the length of the expansion member from proximal end 102 to distal end 104.

Optional features of expansion member 110 include a clear polymeric construction, and a lighting feature that includes self-contained light sources (e.g., bulbs or LED or LCD light emitters) 121 and a power source 123 (e.g., battery or capacitor, etc.). Additionally, proximal end 102 includes handles 124 and 125. Each handle (124, 125) is connected to a side panel and can be moved (independently of the other handle) to rotate the attached side panel relative to the center panel. Expansion member 110 can be used according to the general description, for example, in methods and using method steps as identified for expansion members 10 and 50, herein.

FIGS. 4A, 4B, 4C, and 4D show additional features that may optionally be included as part of an expansion member, such as expansion member 110. As illustrated, proximal end 102 of expansion member 110 includes handles 124 and 125, and, connected to each handle, ratchet 126. Ratchet 126 includes arms 128 and 129, connecting together at and extending from ratcheting joint 130. In use, with ratchet arms 128 and 129 connected to handles 124 and 125 being spread apart, distal end 104 and panels 112, 114, and 116 can be inserted into a patient through an incision or orifice. Side panels 114 and 116 are folded against center panel 112 and expansion member 110 is in a closed configuration. To open expansion member 110 for retracting tissue, handles 124 and 125 are moved toward each other along with arms 128 and 129; arms 128 and 129 rotate about ratcheting joint 130 and arms 128 and 129 rotate about joint 138 and toward each other. As arms 128 and 129 rotate about joint 138, ratchet 126 allows one-way movement in a direction that causes panels 114 and 116 to open (within a patient) to create access space 134 between panels 112, 114, and 116. Ratchet 126 can be released by a release mechanism (not illustrated) at proximal end 102 to allow the panels to fold together, and expansion member 110 to be removed after a surgical procedure.

Also as illustrated, distal end 104 includes distal edge 133 that is situated at an angle relative to longitudinal axis L, when expansion member 110 is viewed from a side. Distal edge 133 is angled or slanted relative to longitudinal axis L in a direction that allows edge 133 to align with a slant of pelvic anatomy at a posterior region of a patient's pelvis, such as at a region of sacral anatomy, while expansion member 110 is installed transvaginally.

Also illustrated, distal edge 133 includes or is composed of a flexible material in the form multiple segmented tips or tissue wipers 135, which are flexible features that can be deflected (e.g., laterally) to conform to tissue when distal end 104 is inserted into a patient and pressed against the tissue. As shown at FIG. 9, these features are in the form of a relatively soft or flexible polymer piece having a "height" that extends substantially vertically along each side panel, and including a series of short cuts in the longitudinal direction at regular intervals along the height. The regularly-spaced longitudinal cuts create a series of longitudinal "fingers" or tissue wiper segments 135 that can be deflected laterally (e.g., left or right) in response to contact with tissue. Segments 135 can be made of a flexible, conformable material that is capable of changing shape (e.g., deflecting or bending) to conform to anatomical tissue such as muscle, bone, or ligaments located at a posterior pelvic region. The flexible, conformable material may be the same as or different than the material used to produce a living hinge, e.g., a non-rigid polymer or foam (open or closed cell) material comprising one or a combination of natural rubber, synthetic rubber, silicone, polyurethane, polyolefin, and the like.

Referring to FIGS. 5A, 5B, 5C, 5D, and 5E, retractor or expansion member 150 includes proximal end 152, distal end 154, and longitudinal panels, 162, 164, 166, and 168. Expansion member 150 is configured for use during a surgical procedure to provide access to a surgical site or anatomy, e.g. transvaginal access to a region of sacral anatomy. Panel 162 is an upper center panel (or top panel) having edges 180 and 182 extending longitudinally between proximal end 152 and 154. Panel 164 is a distal side panel extending longitudinally along a distal portion of the length of expansion member 150, and having edge 184. Panel 166 is a distal side panel extending longitudinally along a distal portion of the length of expansion member 150, and having edge 176. Edges 182 and 184 meet along longitudinal hinge 156. Edges 180 and 176 meet along longitudinal hinge 158. Each of hinges 156 and 158 may be any type of hinge such as a living hinge or a mechanical type of a hinge.

Figure 5A:
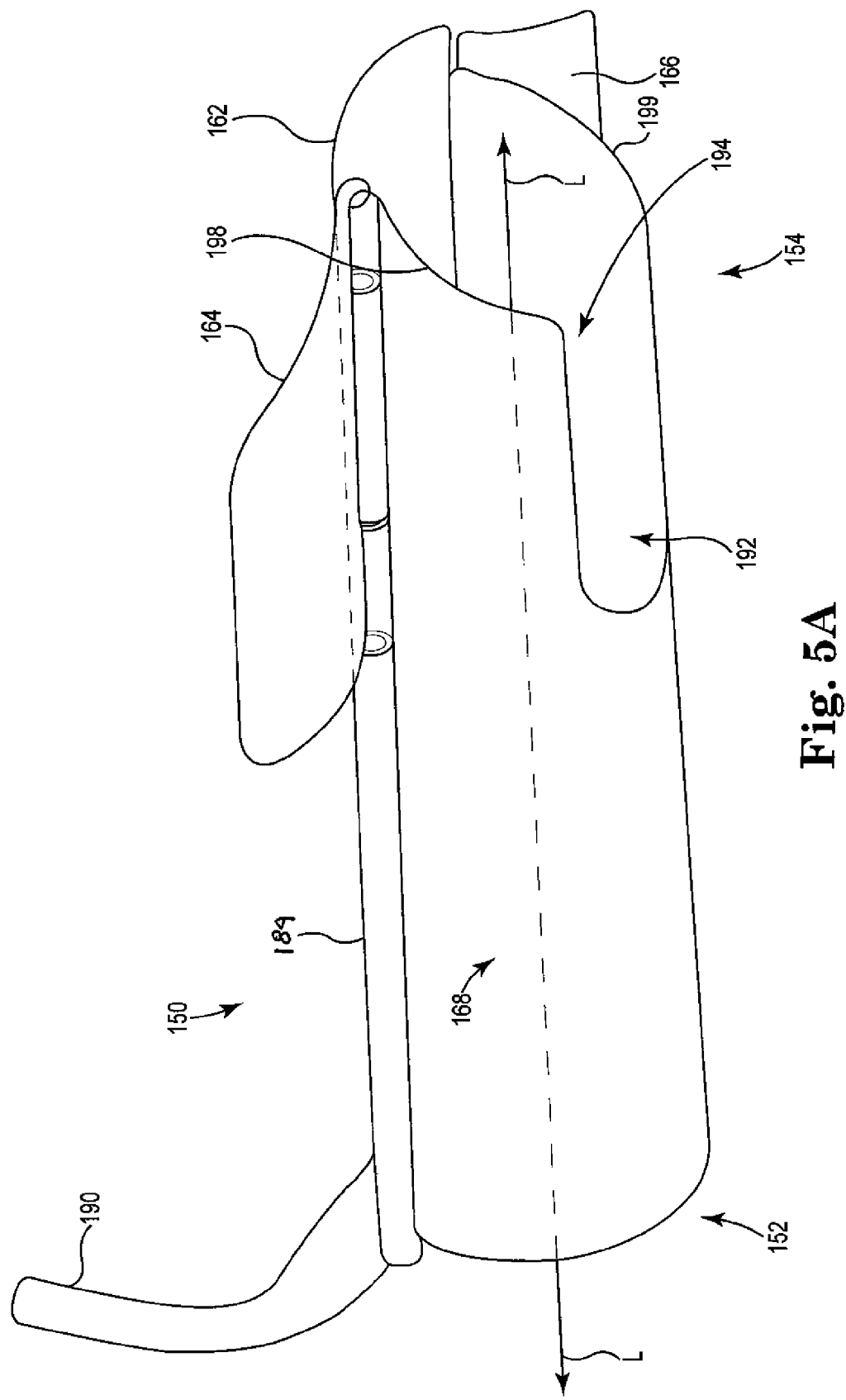
FIG. 5A is a bottom perspective view of an embodiment of an expansion member.
Figure 5B:
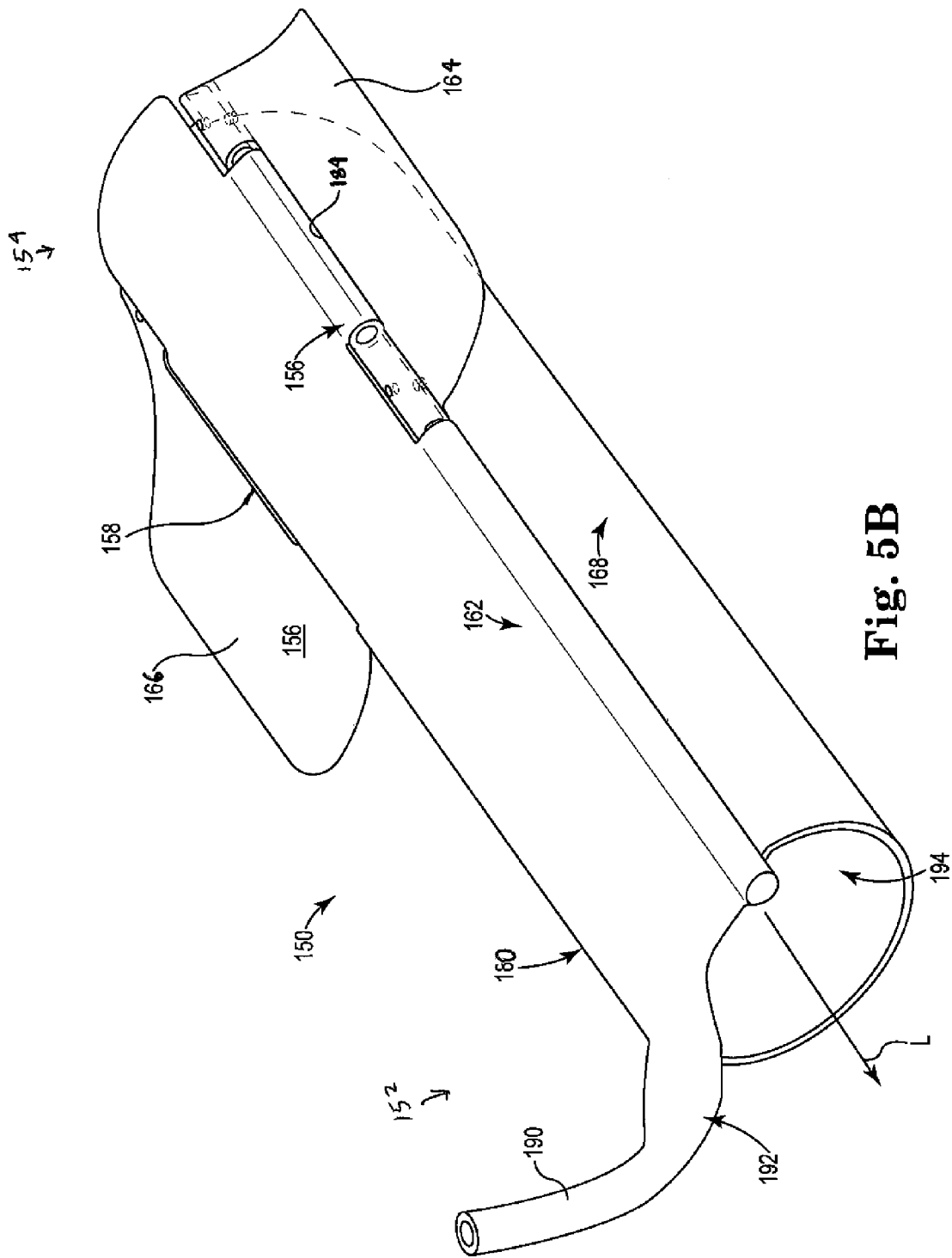
FIG. 5B is a top perspective view of an embodiment of an expansion member.

Panels 162, 164, and 166 can be configured in either an open or a closed configuration. In a closed configuration as illustrated at FIG. 5D, hinges 156 and 158 are closed and distal side panels 164 and 166 (respectively) are folded against (and below, or inferior to) upper center panel 162. From that closed configuration, distal side panels 164 and 166 can be moved by rotating panels 164 and 166 about hinges 156 and 158, respectively, resulting in an open configuration as illustrated at FIGS. 5A, 5B, 5C, and 5E. In the open configuration, hinges 158 and 156 are opened and distal side panels 166 and 164 are spread laterally.

Edges 180 and 182 also engage opposing edges 170 and 172 of bottom panel 168 (see FIG. 5C). With distal panels 162, 164, and 166 in the open configuration, bottom panel 168 can be slidably engaged with center panel 162, e.g., by a slidable engagement between respective opposing edges of center panel 162 and bottom panel 168. As shown in detail at FIG. 5C, bottom panel 168 includes edges 170 and 172, extending longitudinally, that can slidably engage edges 180 and 182 of center panel 162. The adjacent edges of bottom panel 168 and the center panel 162 can be connected by a desired sliding connection, such as opposing channel and bead structures or any useful or equivalent set of opposing sliding engagements (e.g., as described herein with respect to other connected edges).

FIG. 5C shows an embodiment of an exemplary sliding engagement between adjacent edges of lower center panel 168 and side panels 164 and 168. As illustrated, edges 170 and 172 of bottom panel 168 are biased to spread apart; opposing curved outer surfaces of edges 170 and 172 are situated against opposing oppositely-curved internal surface of edges 180 and 182. The combination of fitted curved opposing surfaces and a bias of bottom panel 168 at the upper edges is sufficient to allow a removable slidable connection between edges of panel 162 and edges of panel 168.

Still referring to FIGS. 5A through 5E, expansion member 150 is shown to include optional optical fiber holder 190 and channel 192. A laser-centerline indicator (not shown) could also be included. Channel 192 extends from holder 190 at proximal end 152, in a distal direction along center panel 162 to a location about midway between proximal end 152 and distal end 154. Holder 190 and channel 192 allow for an optical fiber (not shown) to be inserted at proximal end 152 passed through channel 192 in a distal direction along a length of expansion member 150, for placement of the optical fiber to provide light to access space 194, to receive images from access space 194, or both.

Also illustrated as an optional feature of an expansion member, distal end 154 includes distal edge 198 that is situated at an angle relative to longitudinal axis L, when expansion member 150 is viewed from a side. As illustrated, distal edge 198 is angled or slanted relative to longitudinal axis L in a direction that allows edge 198 to align with a slant of pelvic anatomy at a posterior region of a patient's pelvis, such as at a region of sacral anatomy, while expansion member 150 is installed transvaginally.

In use, expansion member 150 can be placed in a closed or folded configuration by folding distal side panels 164 and 66 against the underside of center panel 162 (see FIG. 5D). In the closed configuration, expansion member 150 can be inserted through an incision or body orifice (e.g., into a vaginal introitus and optionally through a transvaginal incision at a posterior of vaginal tissue). Upon placement into a body orifice, expansion member 150 can be converted to an open configuration by unfolding moving distal side panels 164 and 166 away from center panel 162. Side panels 164 and 166 rotate about hinges 156 and 158 (see arrows at FIG. 5D) to cause retraction or movement of tissue adjacent to distal side panels 164 and 166. The location of distal side panels 164 and 166 at a distal portion of expansion member 150, and not extending the entire length of expansion member 150, allows for the side panels to be located (when expansion member 150 is installed transvaginally) to contact and retract tissue that is posterior to vaginal tissue, e.g., tissue located posterior to a vaginal apex or vault, between a vaginal apex or vault and a sacrum, and that may include tissue of a bowel or peritoneum.

Also after placing expansion member 150 through an incision in a patient (e.g., transvaginally), bottom panel 168 can be attached to upper center panel 162 by sliding bottom panel 168 into place within the patient incision and in engagement with edges 180 and 182. Expansion member 150, when assembled to include bottom panel 168 slidably engaged with upper center panel 162, defines access space 194. Proximal end 152 remains external to the patient and distal end 154 passes transvaginally to a location at a posterior pelvic region, e.g., placing distal edge 198 in contact with or adjacent to tissue of a region of sacral anatomy. During or after insertion, expansion member 150 can be opened by unfolding distal side panels 164 and 166, and bottom panel 168 can be installed by sliding into engagement with edges 180 and 182. After the surgical procedure is completed, bottom panel 168 can be slid out of the patient and removed from engagement with center panel 162, distal side panels can be folded against center panel 162, and folded expansion member 150 can be removed from the patient.

An optional feature of an expansion member is one or more curved longitudinal hinge. Referring to FIGS. 6A, 6B, 6C, 6D, and 6E, an example of a retractor (or expansion member) 210 includes proximal end 202, distal end 204, and three longitudinal panels, 212, 214, and 216. Panel 212 is a center panel having edges 220 and 222, and is relatively flat in a single plane. These two opposite longitudinal edges (220, 222) are curved to result in an "hourglass"-type profile of the expansion member (when viewed from a top or a bottom of the expansion member), meaning that the distal end region of the expansion member and the proximal end region are wider than the medial region (see FIGS. 6A, 6B, and 6D). Panel 214 is a side panel having curved longitudinal edge 224, and is relatively flat. Panel 216 is a side panel having curved longitudinal edge 226, and is relatively flat. Edges 222 and 224 meet along longitudinal hinge 230. Edges 220 and 226 meet along longitudinal hinge 231. Each of hinges 230 and 231 may be any type of hinge such as a living hinge (e.g., a flexible polymeric membrane, film, or other connection) or a mechanical hinge. In the open configuration, longitudinal opening (e.g., slot or channel) 234 extends along the length of the expansion member, from proximal end 202 to distal end 204.

Figure 6A:
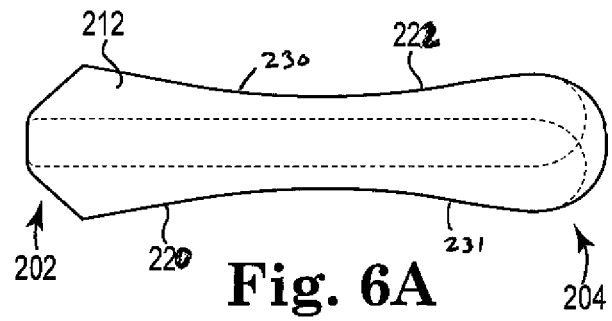
FIG. 6A is a bottom view of an embodiment of an expansion member.
Figure 6B:
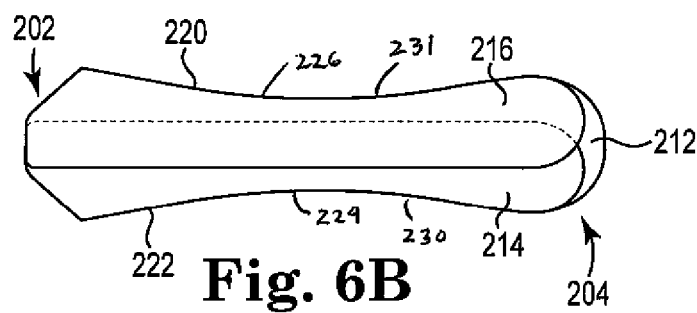
FIG. 6B is a top view of an embodiment of an expansion member.
Figure 6C:
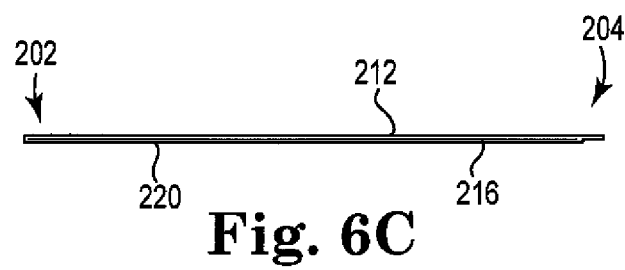
FIG. 6C is a side view of an embodiment of an expansion member.

In a closed configuration, as illustrated at FIGS. 6A, 6B, and 6C, hinges 230 and 231 are closed and side panels 214 and 216 are folded against (and below, or inferior to) center panel 212. As viewed at top view 6A, the shape of the closed expansion member is the same as the shape of center panel 212, having two opposing longitudinal curved edges (220, 222) that produce a widened width dimension at each of the distal and the proximal end regions and a narrowed width dimension at the middle region. As can be seen at FIG. 6C, a side view of expansion member 150 in a closed configuration, the thickness (top to bottom dimension) of expansion member 150 in the closed configuration is relatively small (narrow); because each of panels 212, 214, and 216 is flat, little or no space is present between the folded panels, and the thickness of the folded expansion member is essentially the same as the combined total thickness of the three panels (212, 214, and 216).

From that closed configuration, side panels 214 and 216 can be moved away from center panel 212 by rotating side panels 214 and 216 about hinges 230 and 231, respectively. Upon such movement, rotating each side panel 214 and 216 about 90 degrees to be perpendicular to center panel 212, curved hinges 230 and 231 will produce a curvature or bend in one or more of the panels. When viewed from the bottom as in FIG. 6D, the hourglass profile of center panel 212 remains. When viewed from a side as in FIG. 6E, curved hinges 230 and 231 produce a continuous, curved profile (in dashed line) of center panel 212. Optionally and preferably the curved profile of expansion member 210 (when viewed from the side) in the open configuration can be adapted to conform to anatomy of a patient at a surgical location at which expansion member 210 will be used. Alternately or in addition, the curved profile can be adapted to result in a desired shape of access space 234 when the curved profile is used to retract tissue and gain access to a surgical site, e.g., when placed transvaginally the curved profile of expansion member 210 may advantageously allows improved access to tissue at a region of sacral anatomy, such as tissue at or around a sacrum, sacral promontory, or bowel, peritoneum, or adjacent tissue. Likewise, the curved (hourglass-shaped) profile of center panel 212 can provide for expanded access to tissue at a posterior pelvic region, such as at a region of sacral anatomy, including tissue at or around a sacrum, sacral promontory, bowel, or peritoneum.

Figure 6D:
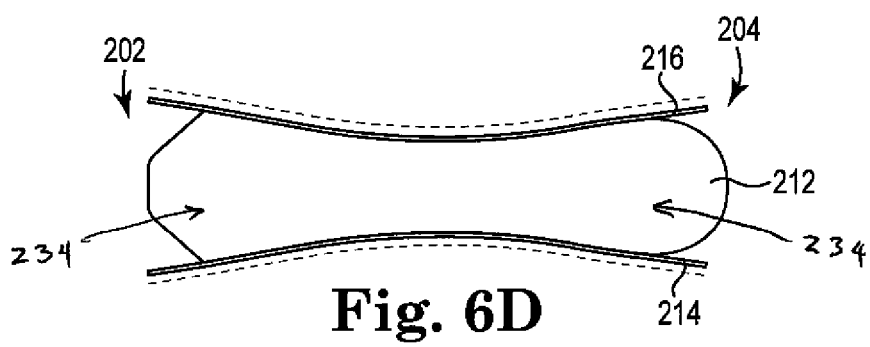
FIG. 6D is a bottom view of an embodiment of an expansion member.
Figure 6E:
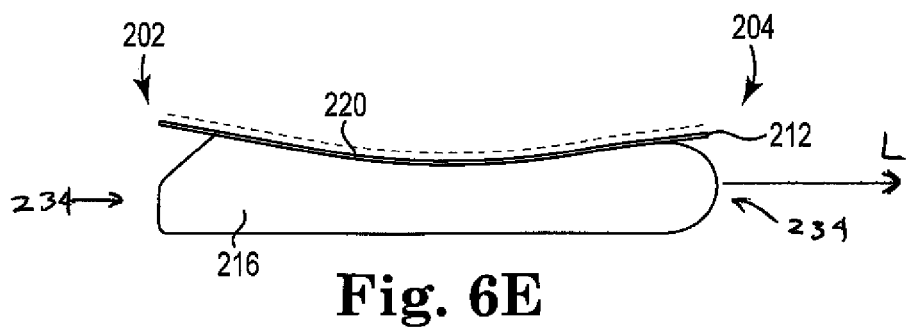
FIG. 6E is a side view of an embodiment of an expansion member.

In the open configuration, as illustrated at FIGS. 6D and 6E, hinges 230 and 231 are opened and side panels 214 and 216 are spread laterally; access space 232 is the longitudinal interior space between opened panels 212, 214, and 216, including longitudinal axis "L."

In use, for example in a transvaginal procedure to access tissue in a region of a sacrum, a surgeon can insert expansion member 210 transvaginally, when expansion member 210 is in the closed configuration. Proximal end 202 remains external to the patient and distal end 204 passes transvaginally to a location at a posterior pelvic region, e.g., at a surgical location of a region of sacral anatomy. During or after insertion, expansion member 210 can be opened by unfolding side panels 214 and 216 to create access space 232 extending from proximal end 202 to distal end 204. After the surgical procedure is completed, expansion member 210 can be folded and removed from the patient.

Figure 7A:
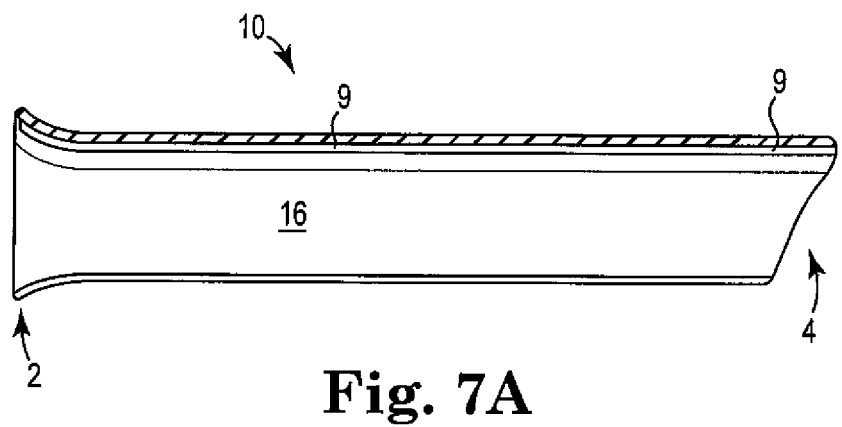
FIGS. 7A and 7B are side and end views of an embodiment of an expansion member.
Figure 7B:
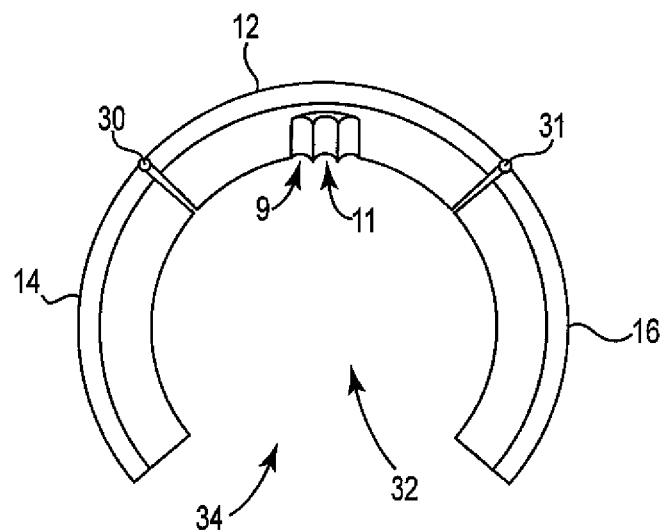

FIGS. 7A and 7B show expansion member 10, similar to that of FIG. 1, and including an additional optional feature of a longitudinal adapter 9 for receiving and securing a coil driver. Coil drivers generally include an elongate, optionally flexible, rotating shaft within a non-rotating sheath, for driving a helical or coil-shaped tissue anchor into tissue of a patient. Examples of coil drivers are described, for example, in WO2011/082350, 61/482,911 and 61/515,638, the entireties of these being incorporated herein by reference. As illustrated, adapter 9 includes receiver 11 located at an inferior surface of center panel 12. Receiver 11 can be in any form useful to securely hold a coil driver, such as a groove, channel, aperture, snap-fitting, locking, or other structure into which an elongate coil driver can be inserted and retained securely for use in driving a coil, screw, bone screw, soft tissue anchor, or other anchoring device, while expansion member 10 is placed within a patient (e.g., transvaginally, or otherwise through a surgical incision). Receiver 11 is illustrated to be a curved, e.g., hemispherical channel, but can be any other form of adapter that can securely retain a coil driver, such as a channel, groove, opening, aperture, a magnet, etc. Preferably, receiver 11 includes a detent, snap-fit engagement, locking engagement, or equivalent mechanism to cause the coil driver to remain securely fastened to the receiver during use.

Figure 8A:
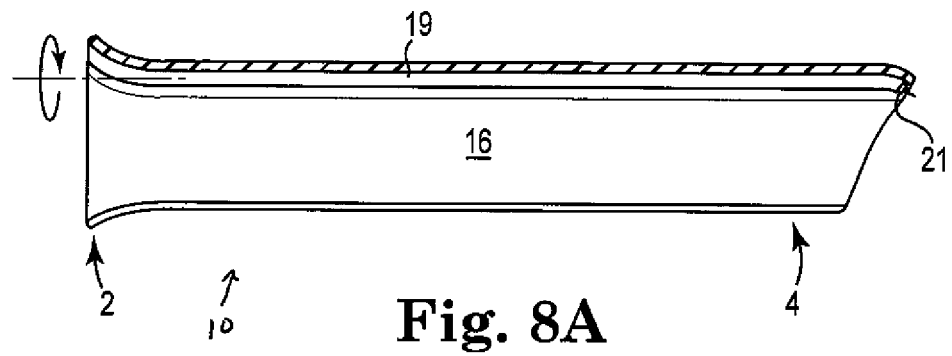
FIGS. 8A and 8B are side and end views of an embodiment of an expansion member.
Figure 8B:
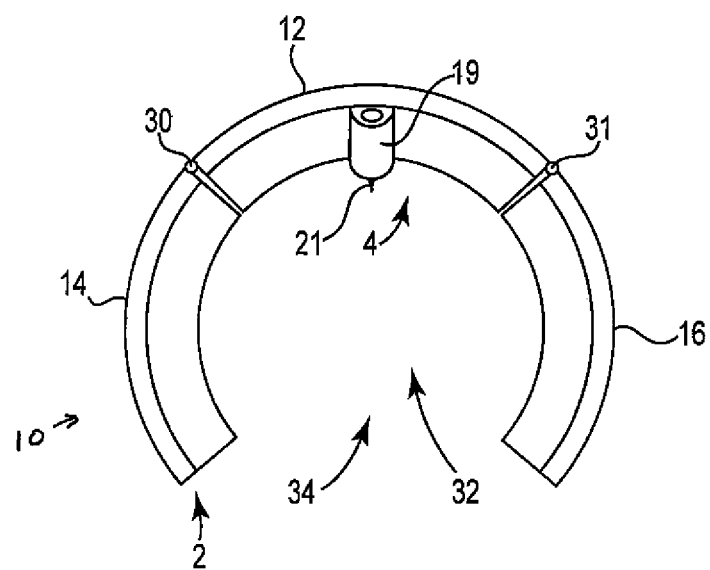

FIGS. 8A and 8B show expansion member 10, similar to that of FIG. 1, and additionally including an optional feature of a coil driver 19 for driving a helical or coil-type tissue (e.g., soft tissue or bone) anchor. Coil driver 19 may generally include an elongate, optionally flexible, rotating shaft within a non-rotating sheath, for driving a helical or coil-shaped tissue anchor into tissue of a patient. As illustrated, driver 19 extends from proximal end 2, along the length and on the underside of center panel 12, to distal end 4, at which location the distal end of a rotating drive shaft is exposed, to engage a helical or coil-type tissue anchor. Driver 19 can be engaged with or constructed integrally with center panel 12 (or another panel), and located to allow the driver to be useful use in driving a coil or other soft tissue anchor into tissue while expansion member 10 is placed within a patient (e.g., transvaginally, or otherwise through a surgical incision).

FIGS. 9A, 9B, 10A, and 10B illustrate other embodiments of expansion members. Expansion member 10 is a one-piece device, not including multiple panels or moveable hinges. Expansion member 10 includes proximal end 2, distal end 4, access space 32, extension 12, distal edge 8, and longitudinal axis L. Expansion member 10 distal end 4 includes distal edge 8 that is situated at an angle relative to longitudinal axis L, when expansion member 10 is viewed from a side (see FIGS. 9B and 10B). Extension 12 at distal end 4 includes distal edge 8 and is made of a flexible, conformable material that is capable of changing shape and conforming to anatomical tissue such as muscle, bone, or ligaments located at a posterior pelvic region. Elongate opening 34 is located at a distal region on a side (e.g., bottom) of expansion member 10, extending from distal edge 8 in a direction toward proximal end 2, but not extending the entire length of the expansion member.

Alternate embodiments of devices useful in a manner similar to expansion members as described are also contemplated for use in providing access to internal tissue of a pelvic region through an incision in a male or female patient, e.g., as a tissue retractor used to gain transvaginal access to a posterior region of a female pelvic anatomy. Any of the generally or specifically described expansion members may be useful according to one or more of the methods described herein for placing an implant to support pelvic tissue, for example a SCP procedure, using any one or more of the herein-described implants, insertions tools, multi-functional tools, anchors, etc.

Various such embodiments of "expansion members" are described herein, and may have general structural and operational features that allow one or more flexible, rigid, or semi-rigid, distal retracting structures to be introduced through an incision (e.g., a vaginal incision) in a closed, compressed, or reduced-size or reduced-diameter state, then the moved, assembled, or expanded to enlarge a cross-sectional size or related space or opening to push tissue aside to create space in and access to a pelvic region with access to desired pelvic anatomy. A preferred size of a device can include a cross sectional dimension (e.g., a width or diameter associated with an opening along a length of the device) in the range from 1 to 5 centimeters, such as from 2 to 4 centimeters, when distal retracting structures are in their the reduced-size configuration. Upon opening, un-compressing, expanding, or assembling, etc., the distal retracting structures, a preferred dimension (e.g., a width or diameter associated with an opening along a length of the device) associated with these structures can be in the range from 2 to 10 centimeters, such as from 3 to 7 centimeters. Also generally, these structures (tubes, retractors, and the like) can include desired length dimensions (from a proximal to a distal end) that can be selected to work with a particular anatomy (male or female) and procedure (anterior repair, posterior repair, etc.). A length of a specific structure (tube, retractor, etc.) useful in a transvaginal method of treating a posterior pelvic condition (e.g., a SCP procedure) can be sufficient to allow the distal end to reach a region of a sacral anatomy as a proximal end remains at or outside of the vaginal introitus. A related dimension is the "working depth" of such a device, which is the distance between the distal end of the device and the vaginal introitus, when installed, and which can be any dimension useful or desired, e.g., from 13 to 18 centimeters. A distance by which the device extends proximally, away from a patient, out of the vaginal introitus, is preferably minimized. Still referring to the use of these devices in transvaginal methods of treatment, another relevant dimension is a "working space" dimension, which is a lateral dimension of an opening at a proximal end of the device, such as a diameter, which may preferably be in a range from 3 to 8 centimeters; in a transvaginal method, this is an approximate diameter of a vaginal introitus held open by a proximal end of the device.

According to exemplary uses of certain described expansion members, including any optional features alone or in combination, a vaginal process to reach a sacral promontory can include:

1—Complete an incision through the vaginal apex (or posterior to the apex) and the peritoneum;
2—Confirm sacral promontory (bone=firm feel, promontory=increased depth with minimal anterior movement);
3—Place the expansion member through the vaginal introitus, through the incision, and advance until the distal edge (e.g., the tip of the distal end) meets the sacrum;
4—Open the expansion member (e.g., at the distal end);
5—Optionally, connect a light source (if an external source is used);
6—A working space to the sacrum has been opened and is lighted.

Also according to embodiments of the methods, implants, tools, and devices described herein, any of the described tools can be used for placing any desired pelvic implant in a male or a female patient, and for any of a large variety of conditions, such as a pelvic condition. The implant can include any structural features useful for such treatment, including any desired size, shape, and optional features such as adjustability and anchoring systems. Any of these features may be previously known, future developed, described herein, or described in documents incorporated herein, for any particular implant and method. For example, some figures and discussions include examples of features of "anchors" (e.g., soft tissue or bone anchors, as these terms are generically and inclusively used) that can be useful according to the methods of placing a surgical implant. An implant that includes or is otherwise secured by any of the anchors described can be useful to treat a pelvic condition in a male or a female patient; as a single and non-limiting example, an implant that includes or uses an anchor as described can be used in a transvaginal SCP procedure to provide support to a vaginal cuff, through an implant that includes the anchor, the anchor being attached at a region of sacral anatomy such as a sacral ligament (e.g., anterior longitudinal ligament, a.k.a. the "anterior ligament" or "longitudinal ligament").

Various devices and methods described herein are advantageous because they facilitate reduction of total procedural time if the patient needs a urinary sling, levator floor support, high apical support (fixation to the sacrum), and anterior or posterior prolapse by combining multiple products into one. The pelvic floor support reduces the long term prolapse recurrence as well as improve the patient's sexual function with the high apical support due to the sacral fixation. Moreover, the various tools and methods allow a physician to use a transvaginal approach and achieve a similar tension as what is currently only achievable in a abdominal or laparoscopic approach to the sacrocolpopexy procedure.

The various systems, apparatus, and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010-0174134, 2010-0298630, 2002/147382, and WO 2011/082350 A1, published 7 Jul. 2011. Accordingly, the above-identified disclosures are fully incorporated herein by reference in their entirety.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. An expansion member comprising:
a proximal end,
a distal end,
sidewalls extending along a length from the proximal end to the distal end, the sidewalls comprising an upper panel, a lower panel, a first side panel, and a second side panel, wherein the first side panel is connected by a first longitudinal hinge to the upper panel and the second side panel is connected by a second longitudinal hinge to the upper panel, the lower panel being coupled to the upper panel at the first longitudinal hinge and the second longitudinal hinge, and
an opening in the sidewalls along a distal portion of the length, the opening extending from the distal end in a direction toward the proximal end,
wherein the distal end is capable of being placed through a vaginal introitus to provide access to a region of sacral anatomy.

2. The expansion member according to claim 1 having an inferior side and a superior side, the inferior side having a length that is less than a length of the superior side such that the distal end of the device is slanted from the superior side to the inferior side to be adapted to conform to a sacrum.

3. The expansion member according to claim 2 wherein the sidewalls extend between the inferior side and the superior side, and wherein the sidewalls are fixed.

4. The expansion member according to claim 1 having an inferior side and a superior side, wherein the sidewalls extend between the inferior side and the superior side, and wherein the sidewalls are curved about a longitudinal axis along a length of the expansion member.

5. The expansion member according to claim 1, wherein the expansion member has a length in a range from 13 and 18 centimeters and a diameter in a range from 3 to 8 centimeters.

6. An expansion member comprising
a proximal end, a medial region, a distal end, a length extending from the proximal end to the distal end, and a plurality of panels including a central panel, a first side panel, and a second side panel, the central panel having a first longitudinal edge and a second longitudinal edge, the first longitudinal edge including a curved portion, the second longitudinal edge including a curved portion, the first longitudinal edge of the central panel being coupled to a longitudinal edge of the first side panel via a first longitudinal hinge, the second longitudinal edge of the central panel being coupled to a longitudinal edge of the second side panel via a second longitudinal hinge, the first side panel being rotatable with respect to the central panel at the first longitudinal hinge, the second side panel being rotatable with respect to the central panel at the second longitudinal hinge, and
the expansion member configured to move between an open configuration in which the first side panel and the second side panel are rotated away from a surface of the central panel to create a space defined by the first side panel, the second side panel, and the central panel, and a closed configuration in which the first side panel and the second side panel are folded against the central panel.

7. The expansion member as recited at claim 6 wherein the first longitudinal hinge is a living hinge.

8. The expansion member as recited at claim 6 wherein the second side panel is disposed between the first side panel and the central panel in response to the expansion member being in the closed configuration.

9. The expansion member as recited at claim 6 wherein a thickness of the expansion member in the closed configuration is substantially the same as a combined thickness of the first side panel, the second side panel, and the central panel.

10. The expansion member as recited at claim 6 wherein the central panel has an hourglass profile.

11. The expansion member as recited at claim 6 wherein the longitudinal edge of the first side panel includes a curved portion.

12. The expansion member as recited at claim 6 wherein the longitudinal edge of the second side panel includes a curved portion.

13. The expansion member according to claim 6 wherein the expansion member has a length in a range from 13 and 18 centimeters, and when placed transvaginally to provide access to a region of sacral anatomy, the expansion member has a diameter in a range from 3 to 8 centimeters.

14. A method of transvaginally performing pelvic surgery to support a vaginal apex, the method comprising:
providing an expansion member, comprising
a proximal end, a distal end, and a length extending from the proximal end to the distal end,
two longitudinal panels extending in the length direction and connected by a longitudinal hinge that is curved along the length, one of the two longitudinal panels being rotatable about the other longitudinal panel at the longitudinal hinge, and
wherein the expansion member is capable of exhibiting an open configuration with the longitudinal panels spaced apart to create a space between the longitudinal panels and having a curved longitudinal profile, and a closed configuration with the longitudinal panels relatively closer together and having a flat longitudinal profile,
inserting the distal end through a vagina introitus,
using the expansion member to provide access to a region of sacral anatomy.

15. The method as according to claim 14, comprising:
while the expansion member is placed through the vaginal introitus, increasing a size of an access space of the expansion member.

16. The method according to claim 14 wherein the method includes a sacral colpopexy.

17. The method according to claim 14, comprising
providing an implant comprising an anchor,
placing the anchor transvaginally through the expansion member, and
securing the anchor to an anterior longitudinal ligament.

18. A method of performing pelvic surgery, the method comprising:
providing an expansion member, the expansion member comprising
a proximal end, a distal end, and a length extending from the proximal end to the distal end,
two longitudinal panels extending in the length direction and connected by a longitudinal hinge that is curved along the length, one of the two longitudinal panels being rotatable about the other longitudinal panel at the longitudinal hinge, and
wherein the expansion member is capable of exhibiting an open configuration with the longitudinal panels spaced apart to create a space between the longitudinal panels and having a curved longitudinal profile, and a closed configuration with the longitudinal panels relatively closer together and having a flat longitudinal profile,
the method comprising,
with the expansion member in the closed configuration, inserting the expansion member into a patient through a vaginal introitus,
with the expansion member placed through the vaginal introitus, opening the expansion member to the open configuration.

* * * * *